(12) United States Patent
Zhang et al.

(10) Patent No.: US 9,146,229 B2
(45) Date of Patent: Sep. 29, 2015

(54) ARRAYS AND METHODS FOR GUIDED CELL PATTERNING

(71) Applicant: University of Washington, Seattle, WA (US)

(72) Inventors: Miqin Zhang, Bothell, WA (US); Mandana Veiseh, Emeryville, CA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 13/846,681

(22) Filed: Mar. 18, 2013

(65) Prior Publication Data

US 2014/0018260 A1 Jan. 16, 2014

Related U.S. Application Data

(60) Division of application No. 12/496,730, filed on Jul. 2, 2009, now abandoned, which is a continuation of application No. PCT/US2008/050307, filed on Jan. 4, 2008.

(60) Provisional application No. 60/883,480, filed on Jan. 4, 2007.

(51) Int. Cl.
*G01N 33/50* (2006.01)
*C40B 20/02* (2006.01)
*C40B 40/02* (2006.01)
*H01L 21/02* (2006.01)
*C40B 60/04* (2006.01)

(52) U.S. Cl.
CPC ............ *G01N 33/5008* (2013.01); *C40B 20/02* (2013.01); *C40B 40/02* (2013.01); *G01N 33/5005* (2013.01); *H01L 21/02164* (2013.01); *C40B 60/04* (2013.01)

(58) Field of Classification Search
CPC ....................................................... G01N 33/50
See application file for complete search history.

(56) References Cited

U.S. PATENT DOCUMENTS

| | | | |
|---|---|---|---|
| 5,536,814 | A | 7/1996 | Ruoslahti |
| 5,776,748 | A | 7/1998 | Singhvi |
| 6,551,940 | B1 | 4/2003 | Ko |
| 7,005,378 | B2 | 2/2006 | Crocker, Jr. |
| 2004/0127025 | A1 | 7/2004 | Crocker, Jr. |

FOREIGN PATENT DOCUMENTS

WO 2006/062871 A2 6/2006

OTHER PUBLICATIONS

Zeto et al. (J. Electrochem. Soc., 1975, pp. 1409-1410).*
Masoud et al. (J. Electrochem. Soc., 1985, 132:2685-2693).*
Proksche et al. (J. Electrochem. Soc., 1992, 139:521-524).*
Alcantar, N.A., et al., "Polyethylene Glycol-Coated Biocompatible Surfaces," Journal of Biomedical Materials Research 51(3):343-351, Sep. 2000.

(Continued)

*Primary Examiner* — Jeremy C Flinders
(74) *Attorney, Agent, or Firm* — Christensen O'Connor Johnson Kindness PLLC

(57) ABSTRACT

Guided cell patterning arrays for single cell patterning are disclosed. The arrays include a plurality of cell adhesion sites that are individually isolated on an inert surface. Each cell adhesion site has one or more cell adhesion peptides having affinity to a cell surface receptor. The inert surface is resistant to cell adhesion.

20 Claims, 19 Drawing Sheets

(56) References Cited

OTHER PUBLICATIONS

Boudreau, N.J., and J.A. Varner, "The Homeobox Transcription Factor Hox $D_3$ Promotes Integrin $\alpha_5\beta_1$ Expression and Function During Angiogenesis," Journal of Biological Chemistry 279(6):4862-4868, Feb. 2004.
Carr, G.L., "Resolution Limits for Infrared Microspectroscopy Explored With Synchrotron Radiation," Review of Scientific Instruments 72(3):1613-1619, Mar. 2001.
Choi, I., et al., "In Situ Observation of Biomolecules Patterned on a PEG-Modified Si Surface by Scanning Probe Lithography," Biomaterials 27(26):4655-4660, Sep. 2006.
Dumas, P., et al., "Imaging Capabilities of Synchrotron Infrared Microspectroscopy," Faraday Discussions 126(discussion 303-11):289-302,2004.
Falconnet, D., et al., "Surface Engineering Approaches to Micropattern Surfaces for Cell-Based Assays," Biomaterials 27(16):3044-3063, Jun. 2006.
Flores, B., IV, et al., "Cell Patterning on Silicon-Gold Chips Using a Highly Selective Protein Patterning Technique," Journal of Undergraduate Research in Bioengineering 3(1):20-24, Jan. 2003.
Hahn, R., et al., "Directed Immobilization of Peptide Ligands to Accessible Pore Sites by Conjugation with a Placeholder Molecule," Analytical Chemistry 75(3):543-548, Feb. 2003.
International Search Report and Written Opinion mailed Jul. 2, 2008, issued in corresponding International Application No. PCT/US2008/050307, filed Jan. 4, 2008, 11 pages.
Jo, S., and K. Park, "Surface Modification Using Silanated Poly(ethylene glycol)s," Biomaterials 21(6):605-616, Mar. 2000.
Knoll, W., et al., "Supramolecular Architectures for the Functionalization of Solid Surfaces," Advances in Biophysics 34:231-251, 1997.
Lan, S., et al., "Surface Modification of Silicon and Gold-Patterned Silicon Surfaces for Improved Biocompatibility and Cell Patterning Selectivity," Biosensors and Bioelectronics 20(9):1697-1708, Mar. 2005.
Lefkovits, J., et al., "Platelet Glycoprotein IIb/IIIa Receptors in Cardiovascular Medicine," New England Journal of Medicine 332(23):1553-1559, Jun. 1995.
Martin, M.C., and W.R. McKinney, "The First Synchrotron Infrared Beamlines at the ALS: Spectromicroscopy and Fast Timing," Proceedings of the 4th Low Energy Electrodynamics in Solids Conference (LEES '99), Pécs, Hungary, Ferroelectrics 249(1):1-10, 2001.
Mooradian, D.L., et al., "Characterization of FN-C/H-V, a Novel Synthetic Peptide From Fibronectin That Promotes Rabbit Corneal Epithelial Cell Adhesion, Spreading, and Motility," Investigative Ophthalmology & Visual Science 34(1):153-164, Jan. 1993.
Office Action mailed Mar. 1, 2012, from U.S. Appl. No. 12/496,730, filed Jul. 2, 2009, 2 pages.
Final Office Action mailed Oct. 18, 2012, from U.S. Appl. No. 12/496,730, filed Jul. 2, 2009, 2 pages.
Papra, A., et al., "Characterization of Ultrathin Poly(ethylene glycol) Monolayers on Silicon Substrates," Langmuir 17(5):1457-1460, Mar. 2001.
Spargo, B.J., et al., "Spatially Controlled Adhesion, Spreading, and Differentiation of Endothelial Cells on Self-Assembled Molecular Monolayers," Proceedings of the National Academy of Sciences of the USA (PNAS) 91(23):11070-11074, Nov. 1994.
Tender, L.M., et al., "Electrochemical Patterning of Self-Assembled Monolayers Onto Microscopic Arrays of Gold Electrodes Fabricated by Laser Ablation," Langmuir 12(23):5515-5518, Nov. 1996.
Veiseh, M., et al., "Guided Cell Patterning on Gold-Silicon Dioxide Substrates by Surface Molecular Engineering," Biomaterials 25(16):3315-3324, Jul. 2004.
Veiseh, M., et al., "Highly Selective Protein Patterning on Gold-Silicon Substrates for Biosensor Applications," Langmuir 18(17):6671-6678, Aug. 2002.
Veiseh, M., et al., "Single-Cell-Based Sensors and Synchrotron FTIR Spectroscopy: A Hybrid System Towards Bacterial Detection," Biosensors and Bioelectronics 23(2):253-260, Sep. 2007.
Andrews, W., "Manuals of Food Quality Control: 4. Microbiological Analysis," FAO Food and Nutrition Paper No. 14, Rev. 1, Food and Agriculture Organization of the United Nations, Rome, 1992.
Folch, a., et al., "Molding of Deep Polydimethylsiloxane Microstructures for Microfluidics and Biological Applications," Journal of Biomechanical Engineering 121(1):28-34, Feb. 1999.
Goormaghtigh, E., et al., "Determination of Soluble and Membrane Protein Structure by Fourier Transform Infrared Spectroscopy," in H.J. Hilderson and G.B. Ralston (eds.), "Sub-Cellular Biochemistry, vol. 23: Physicochemical Methods in the Study of Biomembranes," Plenum Press, New York, 1994, Chap. 8, pp. 329-359.
Hamilton, T.A., et al., "Effects of Bacterial Lipopolysaccharide on Protein Synthesis in Murine Peritoneal Macrophages: Relationship to Activation for Macrophage Tumoricidal Function," Journal of Cellular Physiology 128(1):9-17, Jul. 1986.
Haris, P.I., "Fourier Transform Infared Spectroscopic Studies of Peptides: Potentials and Pitfalls," in B.R. Singh (ed.),."Infrared Analysis of Peptides and Proteins: Principles and Applications," Oxford University Press, Washington, D.C., 1999, Chap. 3, pp. 55-95,1999.
Kandilioti, G., et al., "Molecular Composition and Orientation of Interstitial Versus Surface Silicon Oxides for Si(111)/$SiO_2$ and Si(100)/$SiO_2$ Interfaces Using FT-IR and X-Ray Photoelectron Spectroscopies," Applied Spectroscopy 57(6):628-635, Jun. 2003.
Kirkpatrick, C.J., et al., "Physiology and Cell Biology of the Endothelium: A Dynamic Interface for Cell Communication," International Journal of Microcirculation—Clinical and Experimental 17(5):231-240, Oct. 1997.
Schumann, R.R., et al., "Structure and Function of Lipopolysaccharide Binding Protein," Science 249(4975):1429-1431, Sep. 1990.
Truskey, G.A., and J.S. Pirone, "The Effect of Fluid Shear-Stress Upon Cell-Adhesion to Fibronectin-Treated Surfaces," Journal of Biomedical Materials Research 24(10):1333-1353, Oct. 1990.
Zhang, M., and M. Ferrari, "Enhanced Blood Compatibility of Silicon Coated With a Self-Assembled Poly(ethylene glycol) and Monomethoxypoly(ethylene glycol)," Proceedings of SPIE 3258, Micro—and Nanofabricated Structures and Devices for Biomedical Environmental Applications, Mar. 26, 1998, pp. 15-19.
Akashi, S., et al., "Cutting Edge: Cell Surface Expression and Lipopolysaccharide Signaling via the Toll-Like Receptor 4-MD-2 Complex on Mouse Peritoneal Macrophages," Journal of Immunology 164(7):3471-3475, Apr. 2000.
Aravanis, A.M., et al., "A Genetically Engineered Cell-Based Biosensor for Functional Classification of Agents," Biosensors & Bioelectronics 16(7-8):571-577, Sep. 2001.
Bashir, R., "BioMEMS: State-of-the-Art in Detection, Opportunities and Prospects," Advanced Drug Delivery Reviews 56(11):1565-1586, Sep. 2004.
Bermpohl, D., et al., "Bacterial Programmed Cell Death of Cerebral Endothelial Cells Involves Dual Death Pathways," Journal of Clinical Investigation 115(6):1607-1615, Jun. 2005.
Boudreau, N., et al., "Suppression of ICE and Apoptosis in Mammary Epithelial Cells by Extracellular Matrix," Science 267 (5199):891-893, Feb. 1995. (Author manuscript PMCID: PMC3004777, available in PMC Dec. 20, 2010, 8 pages).
Burke, B., et al., "Macrophages in Gene Therapy: Cellular Delivery Vehicles and In Vivo Targets," Journal of Leukocyte Biology 72(3):417-428, Sep. 2002.
Carter, S.B., "Haptotactic Islands: A Method of Confining Single Cells to Study Individual Cell Reactions and Clone Formation," Experimental Cell Research 48(1):189-193, Oct. 1967.
Chen, C.S., et al., "Cell Shape Provides Global Control of Focal Adhesion Assembly," Biochemical and Biophysical Research Communications 307(2):355-361, Jul. 2003.
Chen, C.S., et al., "Geometric Control of Cell Life and Death," Science 276(5317):1425-1428, May 1997.
Chen, C.S., et al., "Micropatterned Surfaces for Control of Cell Shape, Position, and Function," Biotechnology Progress 14(3):356-363, May-Jun. 1998.
Chiou, P.Y., et al., "Massively Parallel Manipulation of Single Cells and Microparticles Using Optical Images," Nature 436(7049):370-372, Jul. 2005.

(56) References Cited

OTHER PUBLICATIONS

Chittur, K.K., "FTIR/ATR for Protein Adsorption to Biomaterial Surfaces," Biomaterials 19(4-5):357-369, Mar. 1998.
Chiu, D.T., et al., "Patterned Deposition of Cells and Proteins Onto Surfaces by Using Three-Dimensional Microfluidic Systems," Proceedings of the National Academy of Sciences USA (PNAS) 97(6):2408-2413, Mar. 2000.
Cohen, J., "The Immunopathogenesis of Sepsis," Nature 420(6917):885-891, Dec. 2002.
Collier, T.O., et al., "Surface Chemistry Control of Monocyte and Macrophage Adhesion Morphology, and Fusion," Journal of Biomedical Materials Research 49(1):141-145, Jan. 2000.
DeBusschere, B.D., et al., "Portable Cell-Based Biosensor System Using Integrated CMOS Cell-Cartridges," Biosensors & Bioelectronics 16(7-8):543-556, Sep. 2001.
Dubois, L.H., and B.R. Zegarski, "Bonding of Alkoxysilanes to Dehydroxylated Silica Surfaces: A New Adhesion Mechanism," Journal of Physical Chemistry 97(8):1665-1670, Feb. 1993.
Elowitz, M.B., et al., "Stochastic Gene Expression in a Single Cell," Science 297(5584):1183-1186, Aug. 2002.
Flaim, C.J., et al., "An Extracellular Matrix Microarray for Probing Cellular Differentiation," Nature Methods 2(2):119-125, Feb. 2005.
Folch, A., and M. Toner, "Cellular Micropatterns on Biocompatible Materials," Biotechnology Progress 14(3):388-392, May-Jun. 1998.
Folch, A., and M. Toner, "Microengineering of Cellular Interactions," Annual Review of Biomedical Engineering 2:227-256, Aug. 2000.
Folch, A., et al., "Microfabricated Elastomeric Stencils for Micropatterning Cell Cultures," Journal of Biomedical Materials Research 52(2):346-353, Nov. 2000.
Frevel, M.A.E., et al., "p38 Mitogen-Activated Protein Kinase-Dependent and -Independent Signaling of mRNA Stability of AU-Rich Element-Containing Transcripts," Molecular and Cellular Biology 23(2):425-436, Jan. 2003.
Frey, B.L., and R.M. Corn, "Covalent Attachment and Derivatization of Poly(L-lysine) Monolayers on Gold Surfaces as Characterized by Polarization—Modulation FT-IR Spectroscopy," Analytical Chemistry 68(18):3187-3193, Sep. 1996.
Fujihara, M., et al., "Molecular Mechanisms of Macrophage Activation and Deactivation by Lipopolysaccharide: Roles of the Receptor Complex," Pharmacology & Therapeutics 100(2):171-194, Nov. 2003.
Fukai, F., et al., "Modulation of Apoptotic Cell Death by Extracellular Matrix Proteins and a Fibronectin-Derived Antiadhesive Peptide," Experimental Cell Research 242(1):92-99, Jul. 1998.
Gorfti, A., et al., "Covalent and Selective Labeling of Proteins With Heavy Metals. Synthesis, X-Ray Structure, and Reactivity Studies of N-Succinimidyl and N-Sulfosuccinimidyl Ester Organotungsten Complexes," Organometallics 15(1):142-151, Jan. 1996.
Gray, D.S. et al., "Dielectrophoretic Registration of Living Cells to a Microelectrode Array," Biosensors & Bioelectronics 19(12):1765-1774, Jul. 2004.
Gray, S.A., et al., "Design and Demonstration of an Automated Cell-Based Biosensor," Biosensors & Bioelectronics 16(7-8):535-542, Sep. 2001.
Hanein, Y., et al., "Micromachining of Non-Fouling Coatings for Bio-MEMS Applications," Sensors and Actuators B: Chemical 81(1):49-54, Dec. 2001.
Hoshi, T., and M. Kudo, "High Resolution Static SIMS Imaging by Time of Flight SIMS," Applied Surface Science 203-204:818-824, Jan. 2003.
Huang, Y., et al., "Instantaneous, Quantitative Single-Cell Viability Assessment by Electrical Evaluation of Cell Membrane Integrity With Microfabricated Devices," Sensors and Actuators A: Physical 105(1):31-39, Jun. 2003.
Huang, Y., et al., "MEMS-Based Sample Preparation for Molecular Diagnostics," Analytical and Bioanalytical Chemistry 372(1):49-65, Jan. 2002.

Hydén, H., "Isolation and Biochemical Mapping in the Range of $10^{-7}$ to $10^{-12}$ g of Fresh, Single Mammalian Neurons in Brain. II. Some Applications," Trends in Analytical Chemistry 14(4):148-154, Apr. 1995.
Jiang, X., et al., "Electrochemical Desorption of Self-Assembled Monolayers Noninvasively Releases Patterned Cells From Geometrical Confinements," Journal of the American Chemical Society 125(9):2366-2367, Mar. 2003.
Jimbo, et al., "Simulaneous Measurement of Intracellular Calcium and Electrical Activity From Patterned Neural Networks in Culture," IEEE Transactions on Biomedical Engineering 40(8):804-810, Aug. 1993.
Kam, L., and S.G. Boxer, "Cell Adhesion to Protein Micropatterned-Supported Lipid Bilayer Membranes," Journal of Biomedical Materials Research 55(4):487-495, Jun. 2001.
Kao, W.J., et al., "Protein-Mediated Macrophage Adhesion and Activation on Biomaterials: A Model for Modulating Cell Behavior," Journal of Materials Science: Materials in Medicine 10(10/11):601-605, Oct.-Nov. 1999.
Kirkley, J.E., et al., "Temperature Alters Lipopolysaccharide-Induced Cytokine Secretion of RAW 264.7 Cells," Scandinavian Journal of Immunology 58(1):51-58, Jul. 2003.
Kirkpatrick, C.J., et al., "Endothelial Cell Cultures as a Tool in Biomaterial Research," Journal of Materials Science: Materials in Medicine 10(10/11):589-594, Oct.-Nov. 1999.
Kirsh, R., et al., "Drug Delivery to Macrophages for the Therapy of Cancer and Infectious Diseases," Annals of the New York Academy of Sciences 507:141-154, 1987.
Lee, K.-B., et al., "Protein Nanoarrays Generated by Dip-Pen Nanolithography," Science 295(5560):1702-1705, Mar. 2002.
Lehnert, D., et al., "Cell Behaviour on Micropatterned Substrata: Limits of Extracellular Matrix Geometry for Spreading and Adhesion," Journal of Cell Science 117(Pt 1):41-52, Jan. 2004.
Levenson, E., et al., "Infrared Imaging: Synchrotrons vs. Arrays, Resolution vs. Speed," Infrared Physics & Technology 49(1-2):45-52, Sep. 2006.
Lhoest, J.-B., et al., "Characterization of Adsorbed Protein Films by Time of Flight Secondary Ion Mass Spectrometry," Journal of Biomedical Materials Research 57(3):432-440, Dec. 2001.
Lin, Hi., et al., "Cholera Toxin-Induced Modulation of Gene Expression: Elucidation via cDNA Microarray for Rational Cell-Based Sensor Design," Analytica Chimica Acta 457(1):97-108, Apr. 2002.
Lorenzelli, L., et al., "Bioelectrochemical Signal Monitoring of In-Vitro Cultured Cells by Means of an Automated Microsystem Based on Solid State Sensor-Array," Biosensors and Bioelectronics 18(5-6):621-626, May 2003.
Martin, M.C., and W.R. McKinney, "The First Synchrotron Infrared Beamlines at the Advanced Light Source: Microspectroscopy and Fast Timing," in S.M. Mini et al. (eds.), Materials Research Society Symposia Proceedings: Applications of Synchrotron Radiation Techniques to Materials Science IV, San Francisco, Apr. 13-17, 1998, vol. 524, pp. 11-15.
Massia, S.P., and J.A. Hubbell, "Covalent Surface Immobilization of Arg-Gly-Asp- and Tyr-Ile-Gly-Ser-Arg-Containing Peptides to Obtain Well-Defined Cell-Adhesive Substrates," Analytical Biochemistry 187(2):292-301, Jun. 1990.
Massia, S.P., and J.A. Hubbell, "Vascular Endothelial Cell Adhesion and Spreading Promoted by the Peptide REDV of the IIICS Region of Plasma Fibronectin Is Mediated by Integrin $\alpha_4\beta_1$," Journal of Biological Chemistry 267(20):14019-14026, Jul. 1992.
Miller, L.M., et al., "Combining IR Spectroscopy With Fluorescence Imaging in a Single Microscope: Biomedical Applications Using a Synchrotron Infrared Source (Invited)," Review of Scientific Instruments 73(3):1357-1360, Mar. 2002.
Mrksich, M., "A Surface Chemistry Approach to Studying Cell Adhesion," Chemical Society Reviews 29(4):267-273, 2000.
Mrksich, M., "What Can Surface Chemistry Do for Cell Biology?" Current Opinion in Chemical Biology 6(6):794-797, Dec. 2002.
Mrksich, M., et al., "Using Microcontact Printing to Pattern the Attachment of Mammalian Cells to Self-Assembled Monolayers of Alkanethiolates on Transparent Films of Gold and Silver," Experimental Cell Research 235(2):305-313, Sep. 1997.

(56) References Cited

OTHER PUBLICATIONS

Nelson, C.M., "Degradation of Micropatterned Surfaces by Cell-Dependent and—Independent Processes," Langmuir 19(5):1493-1499, Mar. 2003.
Neumann, E., et al., "Perspectives for Microelectrode Arrays for Biosensing and Membrane Electroporation," Bioelectrochemistry 51(2):125-132, Jun. 2000.
Nuzzo, R.G., "Biomaterials: Stable Antifouling Surfaces," Nature Materials 2(4):207-208, Apr. 2003.
Ostuni, E., "Patterning Mammalian Cells Using Elastomeric Membranes," Langmuir 16(20):7811-7819, 2000.
Ostuni, E., "Selective Deposition of Proteins and Cells in Arrays of Microwells," Langmuir 17(21):2828-2834, 2000.
Pancrazio, J.J., "A Portable Microelectrode Array Recording System Incorporating Cultured Neuronal Networks for Neurotoxin Detection," Biosensors and Bioelectronics 18(11):1339-1347, Oct. 2003.
Pancrazio, J.J., et al., "Development and Application of Cell-Based Biosensors," Annals of Biomedical Engineering 27(6):697-711, Nov.-Dec. 1999.
Park, T.H., and M.L. Shuler, "Integration of Cell Culture and Microfabrication Technology," Biotechnology Progress 19(2):243-253, Mar.-Apr. 2003.
Parker, K.K., et al., "Directional Control of Lamellipodia Extension by Constraining Cell Shape and Orienting Cell Tractional Forces," FASEB Journal 16(10):1195-1204, Aug. 2002.
Parker, M.-C., et al., "A Novel Organic Solvent-Based Coupling Method for the Preparation of Covalently Immobilized Proteins on Gold," Protein Science 5(11):2329-2332, Nov. 1996.
Patel, N., et al., "Immobilization of Protein Molecules Onto Homogeneous and Mixed Carboxylate-Terminated Self-Assembled Monolayers," Langmuir 13(24):6485-6490, Nov. 1997.
Pirone, D.M., and C.S. Chen, "Strategies for Engineering the Adhesive Microenvironment," Journal of Mammary Gland Biology and Neoplasia 9(4):405-417, Oct. 2004.
Polla, D.L., et al., "Microdevices in Medicine," Annual Review of Biomedical Engineering 2:551-576, 2000.
Raetz, C.R.H., "Biochemistry of Endotoxins," Annual Review of Biochemistry 59:129-170,1990.
Reininger-Mack, A., et al., "3D-Biohybrid Systems: Applications in Drug Screening," TRENDS in Biotechnology 20(2):56-61, Feb. 2002.
Rovida, E., et al., "TNF-α-Converting Enzyme Cleaves the Macrophage Colony-Stimulating Factor Receptor in Macrophages Undergoing Activation," Journal of Immunology 166(3):1583-1589, Feb. 2001.
Saxena, R.K., et al., "Evidence for Lipopolysaccharide-Induced Differentiation of RAW264•7 Murine Macrophage Cell Line Into Dendritic Like Cells," Journal of Bioscience 28(1):129-134, Feb. 2003.
Scotchford, C.A., "Protein Adsorption and Human Osteoblast-Like Cell Attachment and Growth on Alkylthiol on Gold Self-Assembled Monolayers," Journal of Biomedical Materials Research 59(1):84-99, Jan. 2002.
Singh, B.R. (ed.), "Preface and Chapter 1" in "Infrared Analysis of Peptides and Proteins: Principles and Applications,"ACS Symposium Series, American Chemical Society, DC, Dec. 1999, vol. 750, pp. vii-37.
Singhvi, R., et al., "Engineering Cell Shape and Function," Science 264(5159):696-698, Apr. 1994.
Soler, C., et al., "Lipopolysaccharide-Induced Apoptosis of Macrophages Determines the Up-Regulation of Concentrative Nucleoside Transporters CNT1 and CNT2 Through Tumor Necrosis Factor-α-Dependent and—Independent Mechanisms," Journal of Biological Chemistry 276(32):30043-30049, Aug. 2001.
Stenger, D.A., "Detection of Physiologically Active Compounds Using Cell-Based Biosensors," TRENDS in Biotechnology 19(8):304-309, Aug. 2001.
Svedhem, S., et al., "In Situ Peptide-Modified Supported Lipid Bilayers for Controlled Cell Attachment," Langmuir 19(17):6730-6736, Aug. 2003.
Takayama, S., et al., "Patterning Cells and Their Environments Using Multiple Laminar Fluid Flows in Capillary Networks," Proceedings of the National Academy of Sciences USA (PNAS) 96(10):5545-5548, May 1999.
Teruel, M.N., and T. Meyer, "Parallel Single-Cell Monitoring of Receptor-Triggered Membrane Translocation of a Calcium-Sensing Protein Module," Science 295(5561):1910-1912, Mar. 2002.
Triantafilou, M., and K. Triantafilou, "Receptor Cluster Formation During Activation by Bacterial Products," Journal of Endotoxin Research 9(5):331-335, Oct. 2003.
Ulevitch, R.J., and P.S. Tobias, "Receptor-Dependent Mechanisms of Cell Stimulation by Bacterial Endotoxin," Annual Review of Immunology 13:437-457, 1995.
Van Bergen, A., et al., "Long-Term Stimulation of Mouse Hippocampal Slice Culture on Microelectrode Array," Brain Research Protocols 11(2):123-133, May 2003.
Veiseh, M., and M. Zhang, "Effect of Silicon Oxidation on Long-Term Cell Selectivity of Cell-Patterned Au/SiO$_2$ Platforms," Journal of the American Chemical Society 128(4):1197-1203, Feb. 2006.
Veiseh, M., et al., "Short Peptides Enhance Single Cell Adhesion and Viability on Microarrays," Langmuir 23(8):4472-4479, Apr. 2007.
Veiseh, M., et al., "Two-Dimensional Protein Micropatterning for Sensor Applications Through Chemical Selectivity Technique," Biomedical Microdevices 3(1):45-51, Mar. 2001.
Voskerician, G., et al., "Biocompatibility and Biofouling of MEMS Drug Delivery Devices," Biomaterials 24(11):1959-1967, May 2003.
Wang, N., et al., "Micropatterning Tractional Forces in Living Cells," Cell Motility and the Cytoskeleton 52(2):97-106, Jun. 2002.
Wang, X, and M. Li, "Automated Electrophysiology: High Throughput of Art," ASSAY and Drug Development Technologies 1(5):695-708, Oct. 2003.
Whitesides, G.M., et al., "Soft Lithography in Biology and Biochemistry," Annual Review of Biomedical Engineering 3:335-373, 2001.
Wiklund Fernström, K., et al., "Our Second Touch System: Receptive Field Properties of Unmyelinated Tactile Afferents in Man," Acta Physiologica Scandinavica 167(2):A26, Oct. 1999.
Wood, B.R., et al., "FTIR Microspectroscopic Study of Cell Types and Potential Confounding Variables in Screening for Cervical Malignancies," Biospectroscopy 4(2):75-91, 1998.
Xia, Y., and G.M. Whitesides, "Soft Lithography," Annual Review of Materials Science 28:153-184, Aug. 1998.
Yang, M., et al., "Cellular Microarrays for Chemical Sensing," Sensors and Materials 15(6):313-333, 2003.
Yarmush, M.L., and A. Jayaraman, "Advances in Proteomic Technologies," Annual Review of Biomedical Engineering 4:349-373, 2002.
Yicong, W., et al., "Drug Evaluations Using a Novel Microphysiometer Based on Cell-Based Biosensors," Sensors and Actuators B: Chemical 80(3):215-221, Dec. 2001.
Zhang, H., et al., "Bacterial Lipoprotein and Lipopolysaccharide Act Synergistically to Induce Lethal Shock and Proinflammatory Cytokine Production," Journal of Immunology 159(10):4868-4878, Nov. 1997.
Zhang, M., and M. Ferrari, "Hemocompatible Polyethylene Glycol Films on Silicon," Biomedical Microdevices 1(1):81-89, Sep. 1998.
Zhang, M., et al., "Proteins and Cells on PEG Immobilized Silicon Surfaces," Biomaterials 19(10):953-960, May 1998.
Ziauddin J., and D.M. Sabatini, "Microarrays of Cells Expressing Defined cDNAs," Nature 411(6833):107-110, May 2001.
Ziegler, C., "Cell-Based Biosensors," Fresenius' Journal of Analytical Chemistry 366(6-7):552-559, Mar.-Apr. 2000.

* cited by examiner

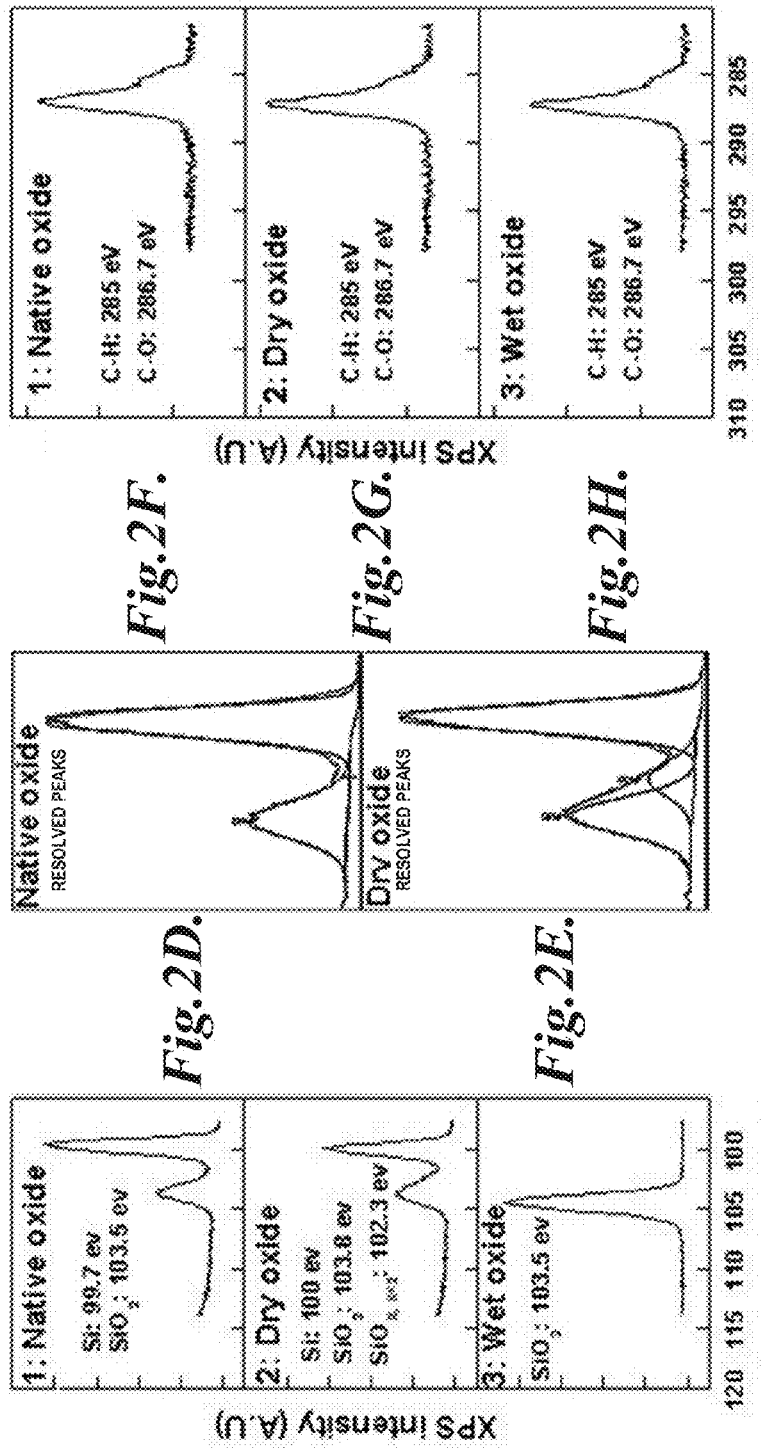

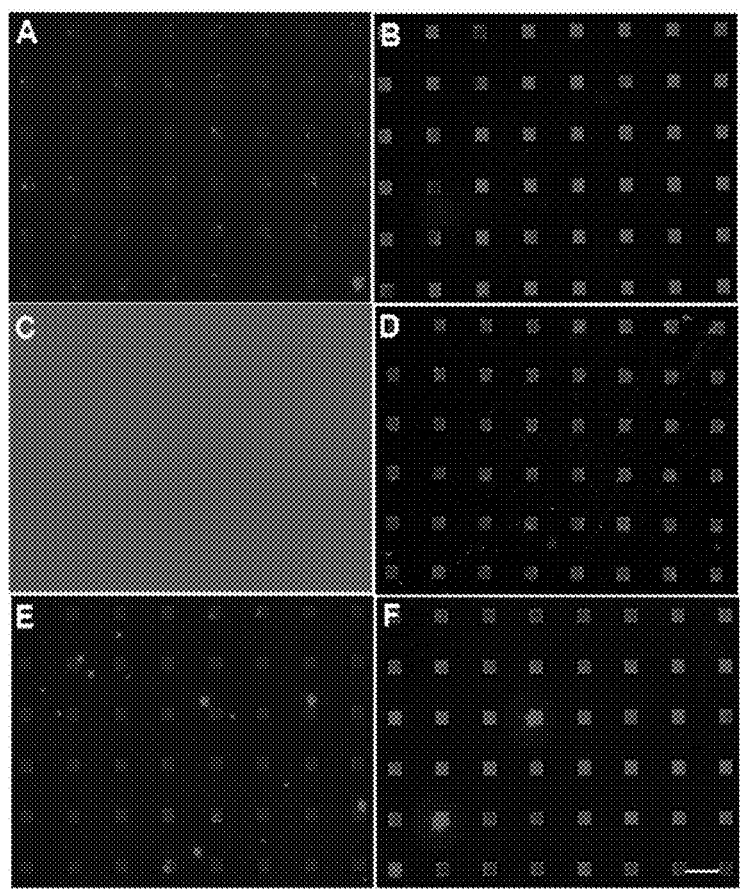
*Fig.3A.* *Fig.3B.* *Fig.3C.* *Fig.3D.* *Fig.3E.* *Fig.3F.*

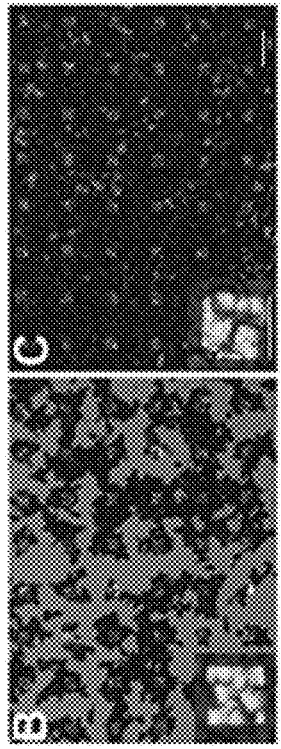
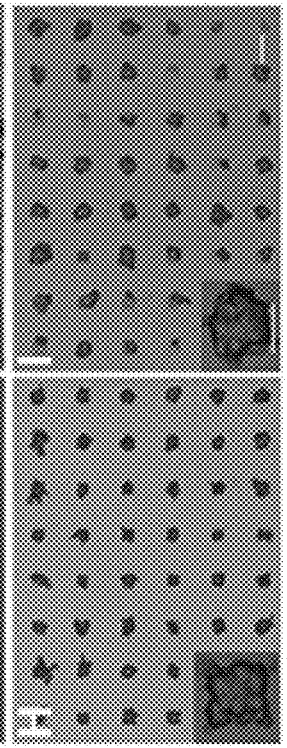
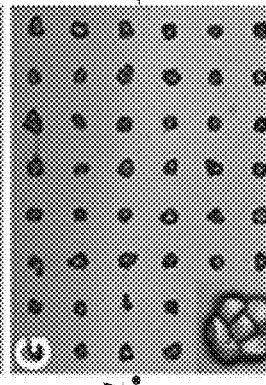
*Fig. 4A.* *Fig. 4B.* *Fig. 4C.*
*Fig. 4D.* *Fig. 4E.* *Fig. 4F.*
*Fig. 4G.* *Fig. 4H.* *Fig. 4I.*

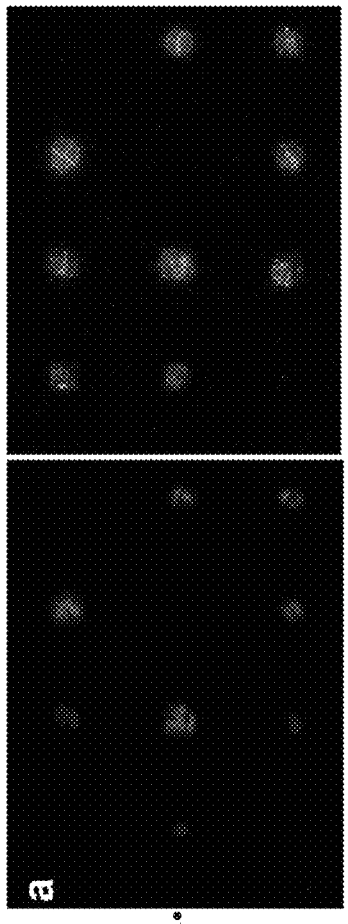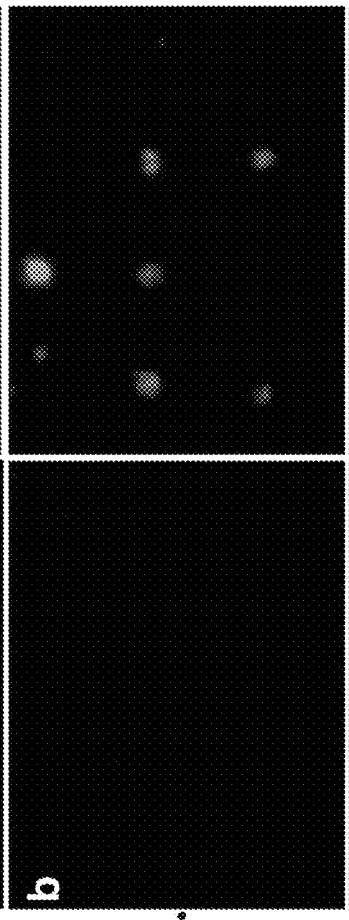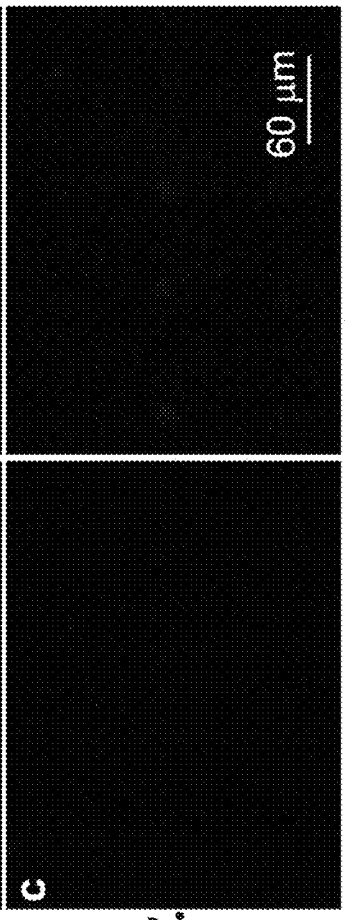
Fig.10A. Fig.10B. Fig.10C. Fig.10D. Fig.10E. Fig.10F.

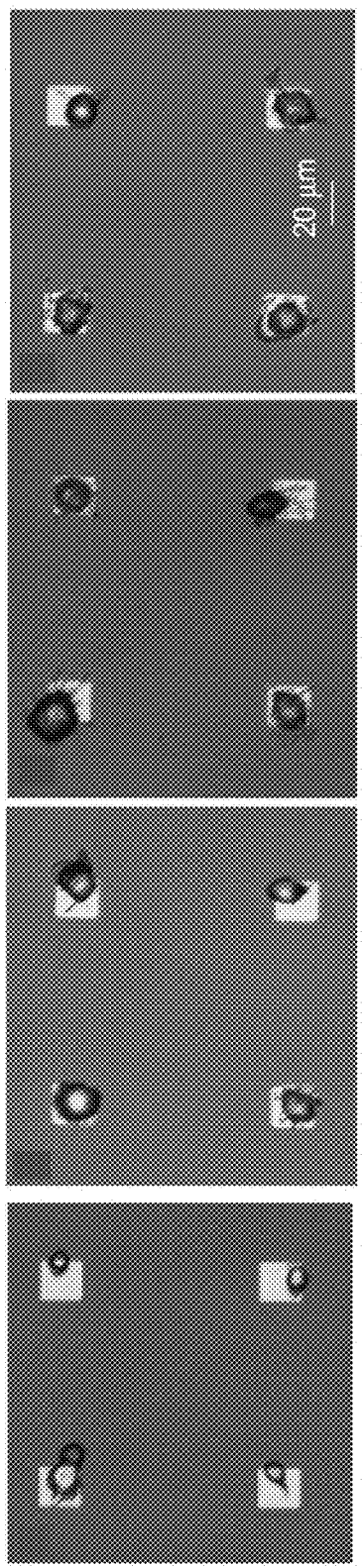

ARRAYS AND METHODS FOR GUIDED CELL PATTERNING

CROSS-REFERENCES TO RELATED APPLICATIONS

This application is a division of application Ser. No. 12/496,730, filed Jul. 2, 2009, which is a continuation of International Application No. PCT/US2008/050307, filed Jan. 4, 2008, which claims the benefit of Provisional Application No. 60/883,480, filed Jan. 4, 2007. Each application is incorporated herein by reference in its entirety.

STATEMENT REGARDING SEQUENCE LISTING

The sequence listing associated with this application is provided in text format in lieu of a paper copy and is hereby incorporated by reference into the specification. The name of the text file containing the sequence listing is 40876_Sequence_Final_2014-05-28.txt. The text file is 4 KB; was created on May 28, 2014, and is being submitted via EFS-Web.

STATEMENT OF GOVERNMENT LICENSE RIGHTS

This invention was made with Government support under Contract No. 5R01GM075095, awarded by the National Institutes of Health and under Contract No. EEC9529161, awarded by the National Science Foundation. The Government has certain rights in the invention.

BACKGROUND OF THE INVENTION

The ability to position and probe a single cell is of great interest in fundamental cell biology, cell-based biosensor technologies, medical diagnostics, and tissue engineering. Because critical cell-to-cell differences are lost in average bulk cell measurements, the single cell analysis with its ability to reveal the response of each individual cell under stimulation is fundamental to comprehending many biological processes and mechanisms. Patterning viable single cells on an addressable array of identical cell hosts, such as an array of microelectrodes with the same physical and chemical properties, would aid the statistical analysis of single cell behavior and cell/matrix interaction. In practical applications, particularly for screening, detection, or sensing systems, microarrays of single cells allow for rapid and inexpensive analysis, require minimal sample volume, and provide high throughput data acquisition and portability.

Cell patterning, micropatterning of living cells on substrates, has experienced a rapid growth in recent years. A number of techniques have been developed to produce microscale cell patterns. Examples include microcontact printing, microfluidic channels, elastomeric stencils, and elastomeric membranes, which involve the delivery of proteins/peptides to guide cell adhesion or direct deposit of cells on a substrate of a single material. Cell patterning can also be achieved by tailoring surfaces to form distinct regions that have adhesive proteins or ligands to host one or groups of cells with a background inert to protein absorption and cell adhesion. Cell patterning can be accomplished via soft lithography (see, for example, Y. Xia and G. M. Whitesides, *Angew. Chem.* 110 (5), 568-594, 1998), photochemistry (see, for example, L. M. Tender et al., *Langmuir* 12:5515-5518, 1996), and photolithography techniques (see, for example, W. Knoll et al., *J. Adv. Biophys.* 34:231-251, 1997). In these techniques, the patterns are formed either by generation of heterogeneous chemistry on a single material or by deposition of a second material in a certain shape and geometry followed by surface modification to form heterogeneous chemistry.

One of the important applications for the cell patterning is for the development of cell-based biosensors (CBBs), in which the patterned regions are miniaturized arrays of metal electrodes and the background is an insulate substrate material. Cell-based biosensors are generally constructed by interfacing cells to a transducer that converts cellular responses into signals detectable by electronic or optical devices. CBBs are hybrid systems of biology and device that use cells' abilities to detect, transduce, and amplify very small changes of external stimuli. Cell-based biosensors offer new opportunities for many medical applications, including biothreat detection, drug evaluation, pollutant identification, and cell type determination.

Recent years have witnessed a substantial growth in application of planar microelectrode arrays in CBBs because they can be readily interfaced with electronic, optical, or chemical detecting means. Major advantages of these sensing arrays over conventional biosensors include rapid and inexpensive analyses, smaller sample size requirement, low sample contamination, high throughput and sensitivity, and portability. Among these sensors, single-cell-based sensors are of particular interest. With an array of virtually identical single cells as sensing elements integrated with real-time data acquisition technology, single-cell-based sensors can be used to experimentally study cellular pathways without interference from other cells, thereby eliminating the uncertainty incurred by states of neighboring cells. In addition, statistical analysis of cell behavior, a topic extensively pursued in cell biology, requires closely identical cell sites, and a single-cell-based system may ideally serve the purpose.

Despite the encouraging advances made with micropatterning of living cells on substrates, patterning single cells on a microarray and retaining their viability for a prolonged period of time remain as a challenge. Single cell patterning requires an area for cell adhesion at a size comparable to an individual cell, which is typically 10 to 20 µm, to minimize the probability of a second cell attachment. However, adhesion sites of such small areas tend to suppress cell spread and thus are prone to causing cell death. It was reported that cells could be geometrically switched between growth and apoptosis. Endothelial cells cultured on single islands coated with fibronectin spread and progressed through the cell cycle when the island area was larger than approximately 40 µm×40 µm, but failed to extend and underwent apoptosis when cells were restricted to areas smaller than approximately 20 µm×20 µm.

A need exists for devices and methods for patterning single cells that allow single-cell adhesion while maintaining cellular viability for a prolonged period of time. The present invention seeks to fulfill these needs and provides further related advantages.

SUMMARY OF THE INVENTION

The present invention provides guided cell patterning arrays, methods for making the arrays, and methods for using the arrays.

In one aspect, the invention provides an array for guided cell patterning. In one embodiment, the array includes a plurality of cell adhesion sites, each site being individually isolated on an inert surface, wherein each cell adhesion site comprises one or more ligands having an affinity to a cell surface receptor; and wherein the inert surface is resistant to cell adhesion.

In one embodiment, each cell adhesion site further comprises a single cell immobilized thereto by the interaction of the one or more ligands and one or more cell surface receptors of the immobilized cell. In another embodiment, each cell adhesion site further comprises two or more cells immobilized thereto by the interaction of the one or more ligands and one or more cell surface receptors of the immobilized cells.

In one embodiment, the inert surface comprises a silicon surface having polyalkylene oxide moieties covalently attached thereto. In another embodiment, the inert surface comprises an oxidized silicon surface having polyalkylene oxide moieties covalently attached thereto.

In another aspect of the invention, methods for making an array of cell adhesion sites is provided. In one embodiment, the method includes:

(a) providing a metal-patterned silicon substrate having an array of metal surfaces disposed on a silicon surface;

(b) forming a self-assembly monolayer on each metal surface to provide an array of monolayers disposed on the silicon surface;

(c) passivating the silicon surface by covalently coupling polyalkylene oxide moieties to the silicon surface to provide a surface resistant to cell adhesion isolating each self-assembly monolayer of the monolayer array; and (d) attaching a plurality of ligands to each self-assembly monolayer to provide an array of cell adhesion sites.

In one embodiment, the method further includes immobilizing a single cell at each cell adhesion site through the interaction of the ligands and one or more cell surface receptors of the cell. In another embodiment, the method further includes immobilizing two or more cells at each cell adhesion site through the interaction of the ligands and one or more cell surface receptors of the cells.

In another aspect, the invention provides methods for analyzing a plurality of single cells immobilized in an array. In one embodiment, the method includes:

(a) subjecting one or more cells individually immobilized in an array to a stimulus to provide an array comprising individually treated cells, the array comprising a plurality of cell adhesion sites, each site isolated on an inert surface, wherein each cell adhesion site comprises a single cell immobilized thereto by the interaction of one or more ligands attached to the site and one or more cell surface receptors of the immobilized cell, and wherein the inert surface is resistant to cell adhesion; and (b) individually addressing one or more of the treated cells to measure the effect of the stimulus on the treated cells.

In one embodiment, individually addressing one or more of the treated cells comprises individually addressing the treated cells optically. In another embodiment, individually addressing one or more of the treated cells comprises individually addressing the treated cells electrically.

In one embodiment, the stimulus is a therapeutic drug compounds. In another embodiment, the stimulus is a toxin.

In a further aspect, the invention provides an array for guided cell patterning having a passivated silicon oxide surface. In one embodiment, the array includes a plurality of individually immobilized cells isolated on an inert surface resistant to cell adhesion, wherein the inert surface comprises a silicon oxide surface having polyalkylene oxide moieties covalently coupled thereto, and wherein the silicon oxide surface comprises from about 40% to 65% by weight Si, from about 5% to about 20% by weight $SiO_{x<2}$, and from about 20% to about 40% by weight $SiO_2$.

In one embodiment, each cell is immobilized through the interaction of one or more ligands and one or more cell surface receptors of the immobilized cell.

In one embodiment, the silicon oxide surface comprises from about 50% to 60% by weight Si, from about 10% to about 15% by weight $SiO_{x<2}$, and from about 25% to about 35% by weight $SiO_2$. In another embodiment, the silicon oxide surface comprises about 58% by weight Si, about 12% by weight $SiO_{x<2}$, and about 30% by weight $SiO_2$.

In another aspect of the invention, methods for making an array for guided cell patterning having a passivated silicon oxide surface is provided. In one embodiment, the method includes:

(a) providing a metal-patterned silicon substrate having an array of metal surfaces disposed on a silicon surface;

(b) exposing the substrate to an oxide etch to remove native oxide from the silicon oxide surface to provide a native oxide depleted silicon surface;

(c) oxidizing the native oxide depleted silicon surface with an oxidizing agent to provide a silicon oxide surface; and (d) passivating the silicon oxide surface by covalently coupling polyalkylene oxide moieties to the silicon oxide surface to provide a surface resistant to cell adhesion isolating each metal surface of the metal surface array.

In one embodiment, the method further includes forming a self-assembly monolayer on each metal surface to provide an array of monolayers isolated on the silicon oxide surface. In another embodiment, the method further includes attaching a plurality of ligands to each self-assembly monolayer to provide an array of cell adhesion sites.

In one embodiment, the further includes immobilizing a single cell at each cell adhesion site through the interaction of the ligands and one or more cell surface receptors of the cell. In another embodiment, the method further includes immobilizing two or more cells at each cell adhesion site through the interaction of the ligands and one or more cell surface receptors of the cells.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

FIGS. 2A-2E compare the high-resolution $Si_{2p}$ spectra of silicon substrates coated with native oxide, dry oxide, and wet oxide; and FIGS. 2F-2H compare the high-resolution $C_{1s}$ spectra of PEG on silicon substrates coated with native oxide, dry oxide, and wet oxide.

FIGS. 3A-3F are the fluorescent images of the fibronectin-Cy3 conjugate adsorbed on surfaces patterned with gold electrodes. FIGS. 3A and 3B show the fluorescent images of the fibronectin-Cy3 conjugate adsorbed on unmodified and PEG-modified surfaces with native oxide on a silicon background, respectively; FIGS. 3C and 3D show the fluorescent image of the fibronectin-Cy3 conjugate adsorbed on unmodified and PEG-modified surfaces with wet oxide on a silicon background, respectively; and FIGS. 3E and 3F show the fluorescent image of the fibronectin-Cy3 conjugate adsorbed on unmodified and PEG-modified surfaces with dry oxide on a silicon background, respectively. Scale bar is 60 μm.

FIGS. 4A-4I are the DIC reflectance microscopic images of macrophage cells cultured on gold-patterned silicon surfaces up to 10 days. FIGS. 4A, 4B, and 4C are images of macrophage cells cultured on gold-patterned silicon surfaces with native oxide on silicon background for 3, 7, and 10 days, respectively; FIGS. 4D, 4E, and 4F are images of macrophage cells cultured on gold-patterned silicon surfaces with wet oxide silicon background for 3, 7, and 10 days, respectively; and FIGS. 4G, 4F, and 4I are images of macrophage cells cultured on gold-patterned silicon surfaces with dry oxide on silicon background for 3, 7, and 10 days, respectively. Scale bars are 60 μm in all low-magnification images and 20 μm in all high-magnification images (insets in all images).

FIG. 5A shows gold squares coated with fibronectin with multiple types of cell adhesion sequences; FIG. 5B shows gold squares coated with physically adsorbed KREDVY and REDVY; and FIG. 5C shows gold squares coated with covalently coupled KREDVY with REDVY.

FIG. 8A shows the trichromatic fluorescence images of the cells stained with DAPI, immunostain (monoclonal anti-vinculin-FITC conjugate), and ALEXA FLUOR 594 phalloidin dye for nuclei, F-actin, and vinculin, respectively. FIG. 8B shows the images of the channel for nuclei; FIG. 8C shows the images of the channel for vinculin; and FIG. 7D shows the images of the channel for actin.

FIG. 9A is the image of HUVE cells cultured on gold-patterned silicon oxide substrates with gold squares coated with fibronectin at 10× objectives; FIG. 9B is the image of HUVE cells cultured on gold-patterned silicon oxide substrates with gold squares coated with physically adsorbed REDVY at 10× objectives; and FIGS. 9C and 9D are the images of HUVE cells cultured on gold-patterned silicon oxide substrates with gold squares coated with covalently coupled KREDVY at 10× objective and 5× objective, respectively. FIG. 9C was captured from FIG. 9D in the area surrounded by the white rectangle. Scale bars are 60 μm in all images.

FIGS. 10A-10F are the fluorescence images of HUVE cells on the gold patterns immobilized with proteins or peptides after 7 days of cell adhesion. FIGS. 10A and 10D are images of cells on the gold patterns immobilized with fibronectin; FIGS. 10B and 10E are images of cells on the gold patterns immobilized with REDVY peptide; and FIGS. 10C and 10F are images of cells on the gold patterns immobilized with KREDVY peptide. FIGS. 10A, 10B, and 10C show the apoptotic cells in fluoresce green; and FIGS. 10D, 10E, and 10F show necrotic cells in fluoresce red. Live cells show little or no fluorescence. Images were taken from triplicate substrates for each type of surfaces.

FIGS. 11A-11D are optical DIC images of macrophage cells cultured on fibronectin-coated electrodes after culture and exposed to LPS for 21 hours. FIG. 11A shows the control cells with no LPS treatment; FIG. 11B shows the cells treated with LPS at concentration of 0.1 μg/mL; FIG. 11C shows the cells treated with LPS at concentration of 1.0 μg/mL; and FIG. 11D shows the cells treated with LPS at concentration of 10 μg/mL.

FIG. 13B shows the image of cells not treated with LPS; FIGS. 13C-13E show the images of cells treated with LPS at concentrations of 0.1 μg/mL, 1.0 μg/mL, and 10 μg/mL for 21 hours, respectively.

FIG. 14A are cell images stained with Annexin V for 15 min; and FIG. 14B are cell images stained with propidium iodide for 15 min.

FIGS. 16A and 16B show FTIR spectra acquired by synchrotron FTIR at the wave number of 3200-3600 cm$^{-1}$ and 1200-1800 cm$^{-1}$, respectively; and FIGS. 16C and 16D show FTIR spectra acquired by conventional FTIR with aperture size as 90 μm×90 μm at the wave number of 2600-4000 cm$^{-1}$ and 1200-1800 cm$^{-1}$, respectively.

DETAILED DESCRIPTION OF THE INVENTION

Figure 1A:
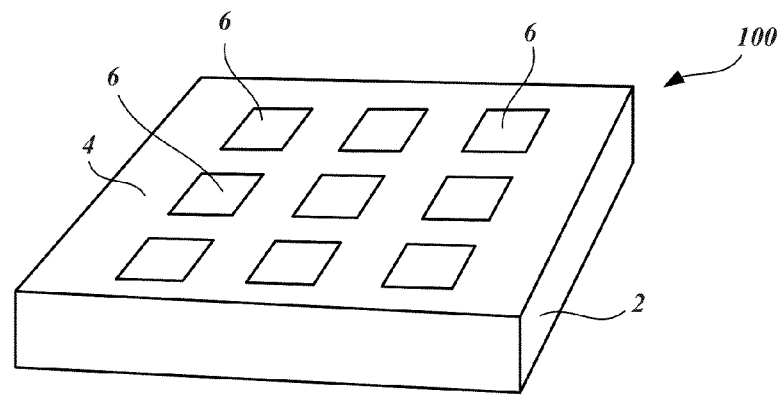
FIG. 1A is a schematic illustration of a representative cell adhesion array of the invention.

The present invention provides guided cell patterning arrays, methods for making the arrays, and methods for using the arrays. The arrays are useful for single cell patterning and provide improved patterning precision, selectivity, stability, and reproducibility.

In one aspect, the present invention provides cell-patterning arrays for guided cell patterning. In one embodiment, the array has a plurality of cell adhesion sites, each site being individually isolated on an inert surface that is resistant to cell adhesion. In the array, each cell adhesion site includes one or more ligands that have an affinity to a cell surface receptor on a cell. Through the use of the ligands immobilized at each site, the arrays of the invention can be used to selectively immobilize desired cells (i.e., ligands can be selected for the site depending on their affinity to cell surface receptors on the cells of interest to be immobilized). The array's inert surface resistant to cell adhesion provides for precise cell immobilization (i.e., cell immobilization only at the adhesion sites).

As used herein, the term "cell adhesion sites" refers to sites on the array that are capable of cell attachment and supporting cell growth. As used herein, the term "inert surface" refers to a surface that is capable of resisting cell adhesion (e.g., by blocking or reducing nonspecific protein interaction). Each individual cell adhesion site is isolated by a portion of inert surface thereby defining an array of cell adhesion sites.

The array's inert surface is a silicon surface that has been passivated (i.e., rendered resistant to cell adhesion) by the attachment (e.g., covalent coupling) of polyalkylene oxide moieties. The polyalkylene oxide moieties may form a self-assembly monolayer on the silicon surface.

In one embodiment, the inert surface is prepared from silicon substrate having a silicon oxide surface. As used herein, "silicon oxide surface" refers to an oxidized surface of a native oxide depleted silicon surface. The silicon oxide surface is prepared by removing native oxide from a silicon substrate surface to provide a depleted native oxide surface followed by oxidizing the depleted native oxide surface. In one embodiment, the silicon oxide surface includes from about 40% to 65% by weight Si, from about 5% to about 20% by weight $SiO_{x<2}$, and from about 20% to about 40% by weight $SiO_2$. In another embodiment, the silicon oxide surface includes from about 50% to 60% by weight Si, from about 10% to about 15% by weight $SiO_{x<2}$, and from about 25% to about 35% by weight $SiO_2$. In a further embodiment, the silicon oxide surface includes from about 58% by weight Si, about 12% by weight $SiO_{x<2}$, and about 30% by weight $SiO_2$. As noted above, the $Si/SiO_{x<2}/SiO_2$ composition of the silicon oxide surface can be achieved by removing the native oxide from a silicon surface to provide a native oxide depleted silicon surface followed by oxidizing the native oxide depleted silicon surface with dry oxygen flow at about 300° C. to about 500° C. for from about 5 to about 24 hours. The preparation of a silicon oxide surface and its conversion to an inert surface of the array of the invention is described below.

The arrays of the invention are used to precisely immobilize select cells. Each cell adhesion site can immobilize one or more cells thereto by the interaction of the one or more ligands and one or more cell surface receptors of the immobilized cells. In one embodiment, each cell adhesion site includes a single cell. In this embodiment, the array is an array of single immobilized cells. Alternatively, each cell adhesion site can include two or more immobilized cells.

Any cell that is viable under cultured conditions can be used in the present invention. Representative cells that can be immobilized to the cell adhesion sites of the arrays of the invention described below include human umbilical cord vein endothelial (HUVE) cells, DAOY cells, glioma cells, and macrophages. Other exemplary cells advantageously immobilized by the arrays and methods of the invention include stem cells, bone cells, muscle cells, and nerve cells, among others. It will be appreciated that the type and nature of the cell immobilized by the arrays and methods of the invention are not limited to those described herein. Any cell having a cell surface receptor that can be immobilized through the interaction of the ligands attached to the cell adhesion site can be advantageously immobilized by the methods described herein to provide the cell-patterned arrays of the invention.

The cell adhesion sites include one or more ligands attached at the site and that act to selectively immobilize cells. The ligand useful for use in a particular array will be selected depending on the cell to be immobilized. Each cell adhesion site presents one or more ligands for immobilizing cells. The ligands are attached to a self-assembled monolayer (e.g., polyalkylene), which is attached to a metal surface on the silicon substrate making up the array platform. The ligands can be adsorbed or covalently coupled to the monolayer.

As used herein, the term "ligand" refers to a substance that binds in a highly specific manner to its cell surface receptor. The term "cell surface receptor" refers to a protein on the cell membrane that binds to the ligand.

In one embodiment, the ligand is a cell adhesion peptide. Representative cell adhesion peptides that can be incorporated into the cell adhesion sites of the arrays of the invention described below include Lys-Arg-Glu-Asp-Val-Tyr (SEQ ID NO:1) (KREDVY) (ligand for human umbilical cord vein endothelial (HUVE) cells), Lys-Arg-Gly-Asp (SEQ ID NO: 2) (KRGD) (ligand for DAOY cells), and Arg-Gly-Asp (RGD) (ligand for cartilage, muscle, and human mesenchymal stem cells). In other embodiments, the cell adhesion peptide is a fragment of fibronectin or a fragment of other cell adhesion proteins.

In one embodiment, the ligand is a peptide. Representative peptides useful as ligands in the invention include chlorotoxin, a 36 residue peptide with high affinity to cells expressing MMP-2 receptors (ligand for rat glioma cells), and nerve growth factor (NGF) (ligand for PC 12 neuronal cells).

In another embodiment, the ligand is a cell adhesion protein. Fibronectin, a cell adhesion protein, is not a ligand for arrays and methods of the invention that do not include a silicon oxide surface as defined herein. Fibronectin is a ligand for arrays and methods of the invention that do include a silicon oxide surface as defined herein.

It will be appreciated that the type and nature of the ligands useful in the arrays and methods of the invention are not limited to those described herein.

Figures 7A, 7B, 7C:
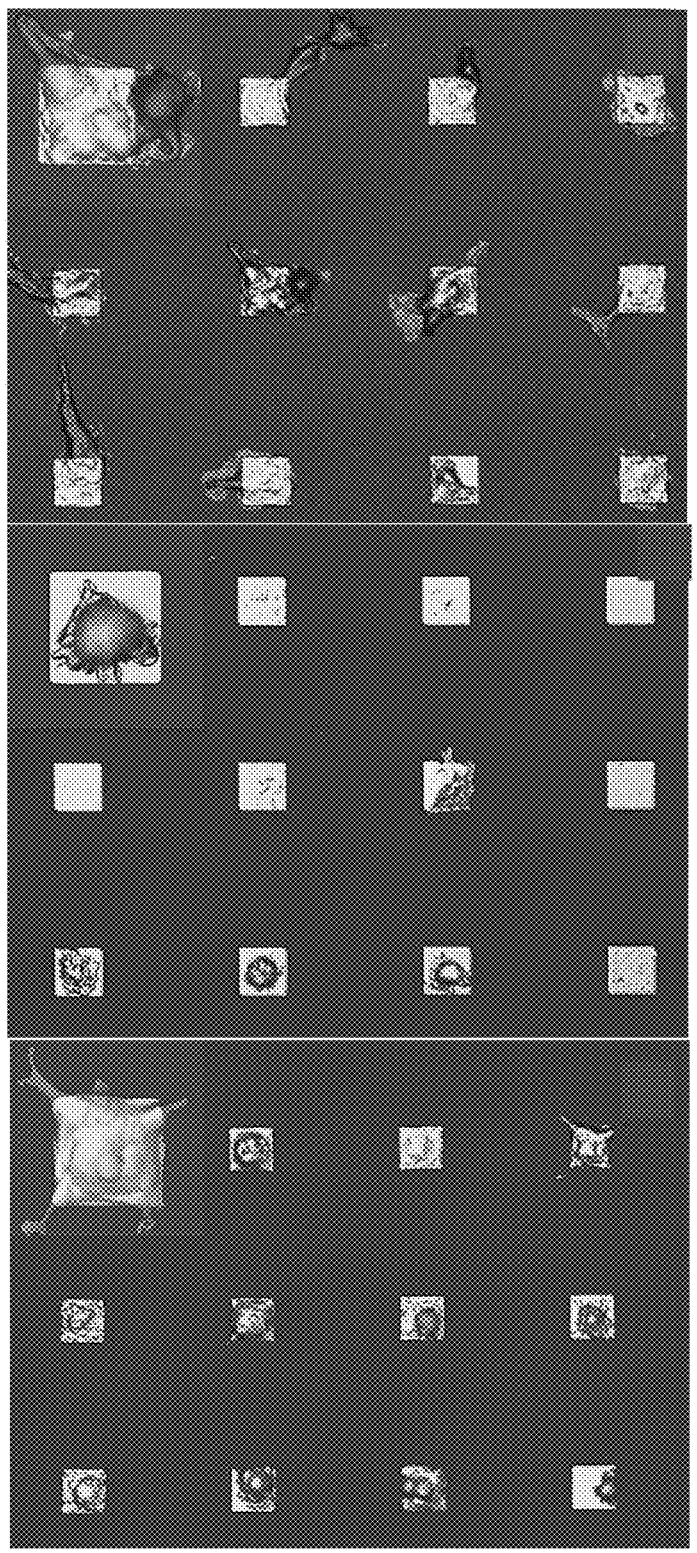
FIGS. 7A, 7B, and 7C show the optical micrographs of HUVE cells patterned on gold electrodes of silicon oxide substrates with gold electrodes coated with fibronectin, physically adsorbed REDVY, and covalently coupled KREDVY, respectively. The insets show a magnified cell image for each case to reveal the cell morphology.
Figures 17, 18, 19:
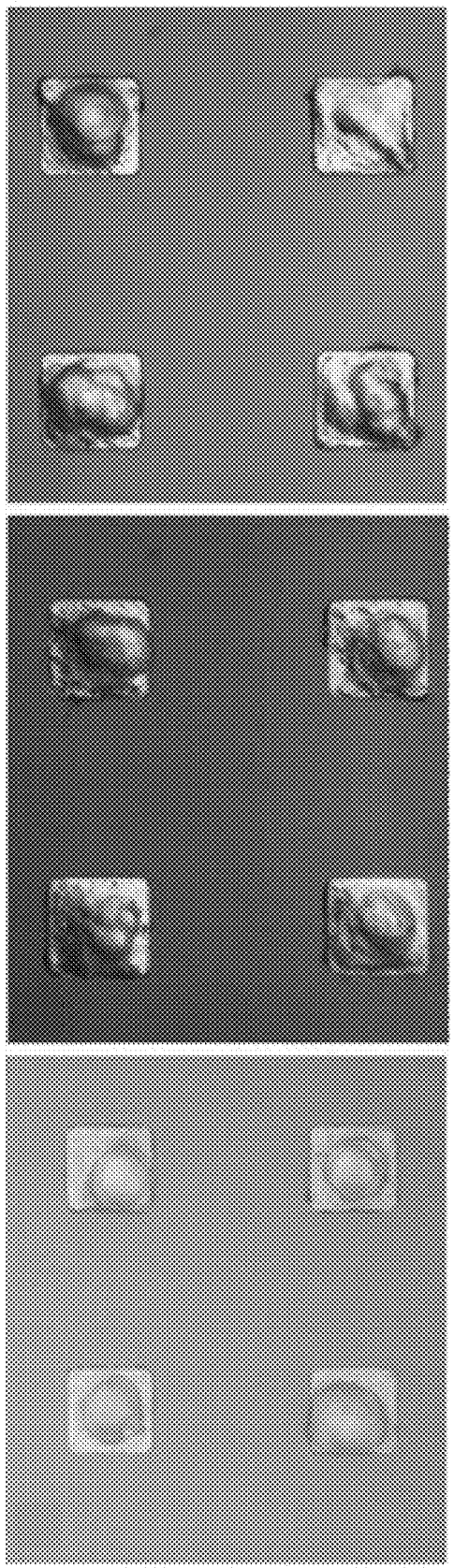
FIG. 17 shows an array of single DAOY cells patterned on 20 μm gold squares covalently bound with Lys-Arg-Gly-Asp (KRGD) peptide.
FIG. 18 shows an array of single 9L (rat glioma) cells patterned on 20 μm gold squares covalently bound with chlorotoxin.
FIG. 19 shows an array of single 6L (glioma) cells patterned on 20 μm gold squares covalently bound with Lys-Arg-Gly-Asp (KRGD) peptide.

A representative array of the invention uses the cell adhesion peptide Lys-Arg-Glu-Asp-Val-Tyr (KREDVY) as the ligand to immobilize human umbilical cord vein endothelial (HUVE) cells. FIG. 7C shows an array of HUVE cells patterned on gold squares covalently bonded with Lys-Arg-Glu-Asp-Val-Tyr peptide. In another embodiment, the cell adhesion peptide Arg-Glu-Asp-Val-Tyr (SEQ ID NO: 3) (REDVY) is the ligand for immobilizing human umbilical cord vein endothelial cells. FIG. 7B shows an array of HUVE cells patterned on gold squares physically adsorbed with Arg-Glu-Asp-Val-Tyr peptide. In another embodiment, the cell adhesion peptide Lys-Arg-Gly-Asp (KRGD) is the ligand for immobilizing DAOY cells. FIG. 17 shows an array of single DAOY cells patterned on 20 µm gold squares and having ligand Lys-Arg-Gly-Asp covalently coupled at the adhesion site. In another embodiment, chlorotoxin is the ligand for immobilizing 9L (rat glioma) cells. FIG. 18 shows an array of single 9L (rat glioma) cells patterned on 20 µm gold squares and having ligand chlorotoxin covalently coupled at the adhesion site. In another embodiment, Lys-Arg-Gly-Asp is the ligand for immobilizing 6L (glioma) cells. FIG. 19 shows an array of single 6L (glioma) cells patterned on 20 µm gold squares and having Lys-Arg-Gly-Asp covalently coupled at the adhesion site. Referring to these figures, the cells are spread over the cell adhesion sites and the inert surface (polyethylene oxide-modified surface) shows no cell adherence.

Figure 1B:
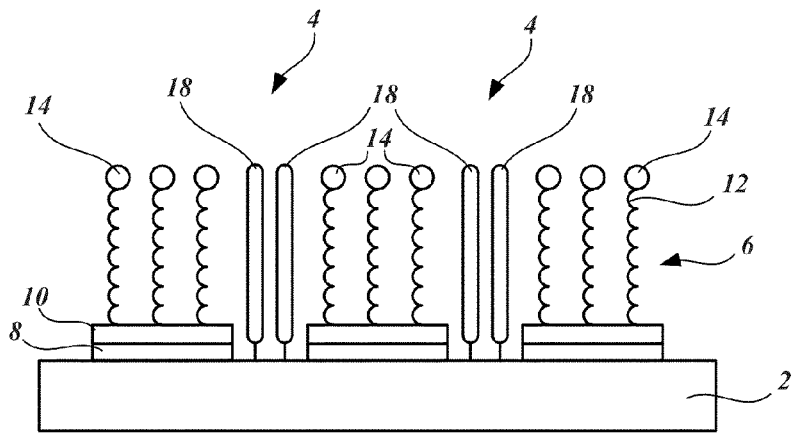
FIG. 1B is a schematic illustration of a representative cell adhesion array of the invention showing array components.
Figure 1C:
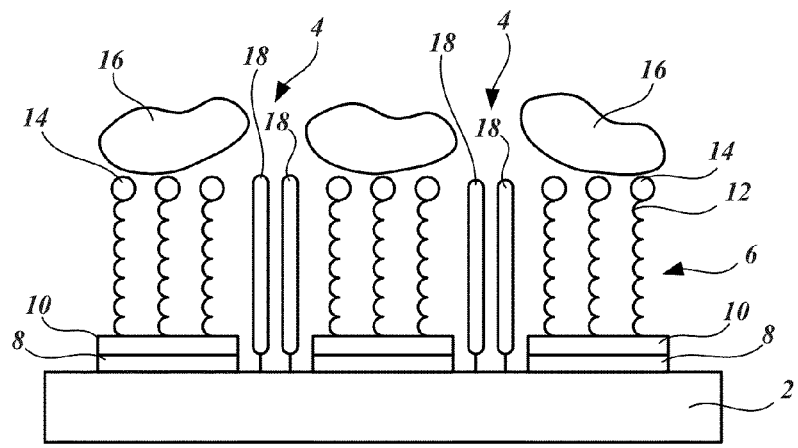
FIG. 1C is a schematic illustration of the array of FIG. 1B showing adhered cells.

A representative array of the invention is illustrated schematically in FIG. 1A. Referring to FIG. 1A, array 100 includes silicon substrate 2 having inert surface 4 individually isolating a plurality of cell adhesion sites 6. The components of a representative array are illustrated schematically in FIG. 1B. Referring to FIG. 1B, cell adhesion sites 6 terminate with ligands 12 that make up self-assembly monolayers at each site. Linkers 12 are coupled to gold surfaces 10. Titanium surfaces 8 are intermediate gold surfaces 10 and substrate 2. Cell adhesion sites 6 are individually isolated (i.e., isolated from each other) by inert surface 4 having polyalkylene oxide moieties 18 coupled to substrate 2. FIG. 1C illustrates a representative single cell patterned array of the invention. Single cells 16 are shown immobilized to sites 6 through ligands 14.

In another aspect, the present invention provides methods for making a cell-patterning array. In one embodiment, the method includes:

(a) providing a metal-patterned silicon substrate having an array of metal surfaces disposed on a silicon surface;

(b) forming a self-assembly monolayer on each metal surface to provide an array of monolayers disposed on the silicon surface;

(c) passivating the silicon surface by covalently coupling polyalkylene oxide moieties to the silicon surface to provide a surface resistant to cell adhesion isolating each self-assembly monolayer of the monolayer array; and (d) attaching a plurality of ligands to each self-assembly monolayer to provide an array of cell adhesion sites.

Each cell adhesion site can include one or more cells immobilized thereto by the interaction of the one or more ligands and one or more cell surface receptors of the immobilized cells. In one embodiment, each cell adhesion site includes a single cell. In this embodiment, the array is an array of single immobilized cells. Alternatively, each cell adhesion site can include two or more immobilized cells.

The silicon surface can be passivated by covalently coupling polyalkylene oxide moieties to the silicon surface. As used herein, the term "passivating" refers to rendering a surface resistant to nonspecific protein adsorption and cell adhesion.

Silanated polyethylene oxide can be used to react with the silicon surface attaching the polyethylene oxide moiety to the silicon surface. In one embodiment, the polyalkylene oxide moieties can be coupled to the surface by exposing the silicon surface to a reactive silane terminated-polyalkylene oxide. Polyethylene oxide moieties can be covalently attached to the silicon surface forming a self-assembly layer (SAM). The choice of catalyst, solvent type, polyethylene oxide chain-length, polyethylene oxide concentration, humidity, temperature, and reaction time can be used to optimize the conditions for forming a uniform monolayer of polyethylene oxide polymers on the oxide surface. In one embodiment, a low molecular weight silanated polyethylene oxide polymer, methoxy-PEG silane (M-PEG-silane, molecular weight=460-590 Dalton, 2-[methoxy(polyethyleneoxy)propyl]trimethoxysilane), was reacted with the silicon surface.

The metal-patterned silicon substrate can comprise a p-type silicon substrate with (100) orientation having an array of metal squares patterned thereon. The metal square can be made from any suitable metal, such as gold, platinum, or silver. In one embodiment, the metal square is a gold square. A titanium square can be deposited on the substrate prior to depositing the gold square. The thickness of the gold square can be from about 50 nm to about 500 nm. The thickness of the titanium layer can be from about 2 nm to about 50 nm.

The metal square can be coated with a self-assembly monolayer. In one embodiment, the method further includes forming a self-assembly monolayer on each metal surface by reacting the metal surfaces with a thiol-terminated alkanoic acid to provide a carboxylic acid-terminated monolayer. In one embodiment, the thiol-terminated alkanoic acid is a C3-C25 alkanoic acid. In one embodiment, the thiol-terminated alkanoic acid is 3-mercaptopropionic acid. In another embodiment, the thiol-terminated alkanoic acid is 11-mercaptoundecanoic acid.

Ligands (e.g., cell adhesion peptides) are attached to monolayer to provide cell adhesion sites. The ligands can be covalently coupled to the self-assembly monolayer through amide bonds formed by the reaction between the terminal carboxylic acid groups on the self-assembly monolayer and the amino groups of the ligands (e.g., the lysine amino for a cell adhesion peptide). Alternatively, the ligands may be physically adsorbed to the self-assembly monolayer.

The preparation of a representative cell-patterning array of human umbilical cord vein endothelial (HUVE) cells is described in Example 1. Endothelial cells play an important role in angiogenesis and tissue repair, and have a broad range of application in detection of bacteria, virus, and toxins. Endothelial cells serve as major barriers separating the blood from tissue compartments whose interaction with bacteria defines the course of invasive infections and inflammatory responses.

A patterned gold/silicon oxide-based cell-patterning platform was prepared according to the method of the present invention. Silicon substrates were cleaned with piranha at 120° C. for 10 minutes, dipped in HF and rinsed with DI water thoroughly. A layer of positive photoresist was then coated on the surface and an array of gold square was patterned on the silicon oxide substrate by conventional microfabrication. Specifically, a layer of titanium (Ti) was deposited onto photoresist-developed substrates. A gold film was subsequently deposited onto the titanium. The photoresist was dissolved and the remaining metal film was lifted off. After lift-off, the surfaces were exposed to buffered oxide etch and rinsed with water to remove the native oxide on silicon regions followed by oxidation with dry air to provide dry oxide surfaces.

The gold squares were chemically modified by reacting COOH-terminated alkyl thiols with the gold layer to afford a surface coated with a COOH-terminated self-assembly monolayer (SAM). The dry oxide surface was passivated with a PEG coating to afford the inert region, which is resistant to nonspecific protein adsorption and cell adhesion. The platforms were then exposed to (a) fibronectin, (b) Arg-Glu-Asp-Val-Tyr (REDVY), or (c) Lys-Arg-Glu-Asp-Val-Tyr (KREDVY), which are used to mediate single cell adhesion and maintain cellular viability. Three platforms with cell adhesion regions containing covalently bound fibronectin and KREDVY and physically adsorbed REDVY were obtained. The platform having fibronectin as an adhesion protein and the platform with physically bound REDVY are used as control platforms.

Figure 5A:
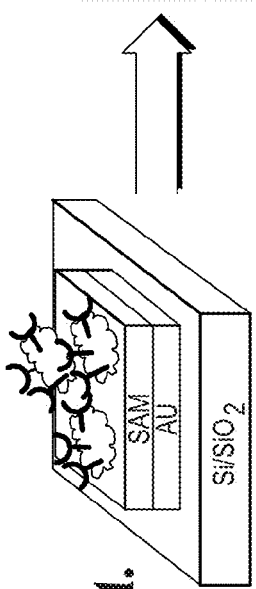
FIGS. 5A, 5B, and 5C are schematic representations of gold squares coated with proteins or peptides.
Figure 5B:
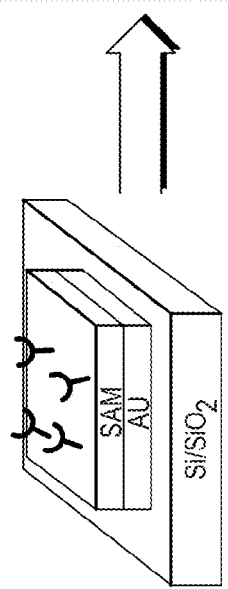
Figure 5C:
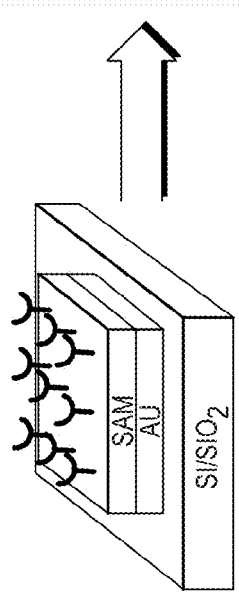

The cell adhesion sites, gold squares coated with fibronectin, REDVY, or KREDVY peptide, are schematically illustrated in FIGS. 5A, 5B, and 5C, respectively. Fibronectin and KREDVY with lysine residues (K) containing s-amino groups were covalently bound to the COOH-terminated SAM on the gold squares. This bonding was formed by activation of the terminal carboxylate group with an N-hydroxysuccinimide (NHS) ester intermediate followed by the displacement of the NHS group by the lysine residue of proteins or peptides. Lacking a reactive lysine residue, REDVY was physically adsorbed onto the gold square. These processes produced three patterned surfaces of different surface chemistries and cell-binding nature, each with an array of cell-adhesive regions (gold squares) on a non-adhesive background (inert regions, passivated silicon oxide) as shown in FIGS. 5A, 5B, and 5C.

Figure 6:
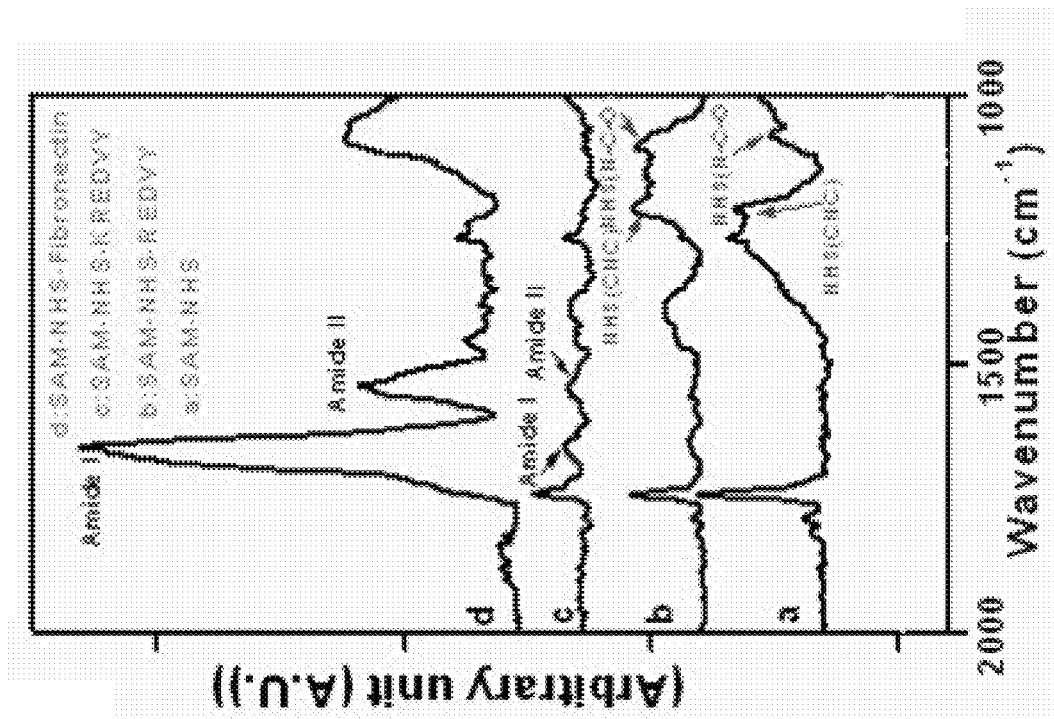
FIG. 6 compares the grazing angle FTIR absorption spectra of surfaces with the coating: (a) NHS ester terminated self-assembly monolayer; (b) physically adsorbed REDVY on the self-assembly monolayer; (c) covalently coupled KREDVY on self-assembly monolayer; (d) covalently coupled fibronectin on the self-assembly monolayer.

The surface chemistries and binding properties of three platforms were characterized by reflectance FTIR spectroscopy. FIG. 6 shows the IR spectra acquired from the surfaces coated with (a) SAM-NHS, (b) SAM-NHS-REDVY, (c) SAM-NHS-KREDVY, and (d) SAM-NHS-fibronectin. Spectrum (a) has characteristic bands at 1078, 1222, 1370, and 1741 $cm^{-1}$, obtained from the surface modified with SAM-NHS, a monolayer on which the protein or peptides were further immobilized. The high intensity band at 1741 $cm^{-1}$ is attributed to asymmetric stretch of NHS carbonyls, and indicates successful covalent binding of NHS with the underlying alkyl thiol SAM. The amide I and amide II peaks in spectrum (b) indicate the presence of associated peptide bonds on the surface. Physical adsorption of REDVY on the surface is confirmed by the presence of unreacted NHS groups with spectrum bands corresponding to vas (CNC) and v (NCO) of NHS at 1222 $cm^{-1}$ and 1078 $cm^{-1}$ that would be otherwise absent due to the chemical bonding. Successful covalent binding between the lysine residue of KREDVY and NHS monolayer is characterized by the presence of the amide I and amide II bands at 1653 and 1543 $cm^{-1}$ (spectrum (c)), the significant reduction of the intensity of carbonyl peak at 1741 $cm^{-1}$ as well as the absence of bands at 1078, 1222, and 1370 $cm^{-1}$ that correspond to NCO stretch, asymmetric CNC stretch, and symmetric CNC stretch of the NHS, respectively. However, the continued presence of a small peak at 1741 $cm^{-1}$ suggests the incomplete conversion of SAM carboxylic groups to amides. Spectrum (d), acquired from the fibronectin-modified surface, confirms the covalent interactions of fibronectin with NHS-SAM. A full conversion of carboxylic groups to amides is characterized by the complete absence of peaks at 1741 $cm^{-1}$ and 1222 $cm^{-1}$ and the presence of strong amide I and amide II peaks. The high intensities of amide I and amide II bands indicate a high density of peptides on the surface, presumably due to the large amount of peptides in fibronectin.

To create microarrays of cell patterns, HUVE cells were cultured on cell-patterning platforms with fibronectin or peptide in standard culture media for 18 hours. After cell culture, the cells were fixed and examined using differential interference contrast (DIC) reflectance optical microscopy. Both REDVY and KREDVY contain tetrapeptide REDV sequence specific to α4β1 receptors of HUVE cells. Fibronectin has at least two types of cell binding sequences for HUVE: the Arg-Gly-Asp (RGD) that would bind to the α5β1 and αvβ3 integrin receptors, and the tetrapeptide REDV that would bind to α4β1 receptors. When immobilized on the COOH-terminated gold surfaces, these cell adhesion protein and peptides would exhibit different binding domain configurations as shown conceptually for a gold-based cell adhesive region in FIGS. 5A-5C. Because fibronectins are long-chain molecules, they would bind to the surface with random orientation of RGD and REDV domains as shown in FIG. 5A, whereas short-chain REDVY and KREDVY peptides would exhibit much more ordered distribution and/or orientation as shown in FIGS. 5B and 5C. Additionally, the KREDVY peptide would exhibit a more uniform molecular orientation as a result of its covalent bonding with the underlying SAM layer and thus provide more uniform binding domains. FIGS. 7A, 7B and 7C show the optical images of HUVE cells adhered on the gold-based cell adhesive regions with fibronectin, REDVY, and KREDVY, respectively. The cells were seen to adhere mainly on the sites of gold-based cell adhesive regions, indicating a high degree of cell selectivity for all three platforms. The cell adhesive regions with bound fibronectin exhibited a pattern of multiple-cell binding on gold squares and slight nonspecific cell adhesion onto the silicon oxide-based inert regions around the cell adhesive regions. This is not surprising in light of the multiple types of cell binding sequences and randomly oriented binding domains of long-chain fibronectin protein. Cell adhesion, the morphology of adhered cells, and the extent of cell spreading are dictated by the availability, conformation, and distribution of cell binding domains. When a cell approaches a gold-based cell adhesive region covered with fibronectin protein molecules, it is confronted with binding domains of different types and orientations. It is conceivable that only a portion of the surface-bound protein molecules and a portion of peptide sequences in those molecules are involved in the cell binding process, presumably those cell binding sequences in the molecules that are oriented roughly at the same direction. Thus, the "effective" binding domains on a gold-based cell adhesive region for the adhesion of this particular cell can be only a small fraction of those physically presented on the gold square. A large number of cell binding sequences in fibronectin does not necessarily result in a large number of effective binding domains, due to the molecules bound in a random orientation to the surface. The spreading of the adhered cell over the gold-based cell adhesive region can also be hindered by the limited number of effective binding domains. Instead, the probability of binding a second cell to the same cell adhesive region is increased due to availability of free binding domains of different types and orientations.

Cells attached on the platform with physically adsorbed REDVY peptide exhibited a pattern with most of gold-based cell adhesive regions hosting one cell (FIG. 7B), but with apparently low cell coverage (the number of cell adhesive regions occupied by cells versus the total number of cell adhesive regions). In addition, the cells barely spread across the gold squares. Two possibilities may account for this low cell coverage, both because of the weak physical binding between the REDVY peptide molecules and underlying SAM-NHS layer: (1) the detachment of REDVY peptide from the gold surface, resulting in an insufficient number of REDVY peptides available on the gold square-based cell adhesive region to bind a cell; (2) the detachment of the cell-REDVY conjugates from the gold square-based cell adhesive region after the cell bound to the REDVY peptides. Low cell spreading on the REDVY-modified platform can also be attributed to the physical binding of REDVY molecules. Cell spreading or migration requires the dynamic formation and dispersal of cell contacts with the extracellular matrix. For receptor-mediated cell adhesion, cell spreading on a surface is driven by the traction force set by adhesive molecules peripheral to the initial focal contacts between the cell and surface. As cell spreading proceeds, which continually stretches the cell and increases force, greater force is required to cause increased cell spreading. A straightforward explanation is that the physically-adsorbed REDVY molecules are unlikely to sustain such traction; instead, they are prone to be detached from the surface by the contractile force of the cell, resulting in the detachment of the REDVY molecules from the surface. Although the physically adsorbed REDVY peptides do not form robust binding with the underlying SAM, they do provide more effective and uniformly distributed binding sites than fibronectin due to their small molecular size. Thus, the majority of REDVY molecules on the gold square-based cell adhesive region would participate in binding of the cell if they are not detached from the surface. Thus, after a cell has been bound, there would be too few binding domains left for binding of a second cell.

On the platform with chemically bound short KREDVY peptide, highly specific single-cell adhesion and higher cell coverage were observed (FIG. 7C). As shown in FIG. 7C, this platform has the most uniform and robust cell binding sites as a result of the covalent binding of KREDVY molecules on the platform. In addition to having all the advantageous properties of the REDVY-modified platform for cell binding, the covalently bound KREDVY is less susceptible to detachment. The fully spread cell morphology suggests that most of the available binding domains on the gold square-based cell adhesive region have participated in the cell binding, and that the covalently bound KREDVY peptide provides sufficient traction force for cell spreading. Thus, once a cell is bound to the gold square-based cell adhesive region, there would remain insufficient free space or binding domains for adhesion of a second cell. Small peptides have additional advantages over proteins in that they are less susceptible to cellular proteolysis and thermal degradation, and thus most of their active domains are available for cell adhesion.

Figure 8A:
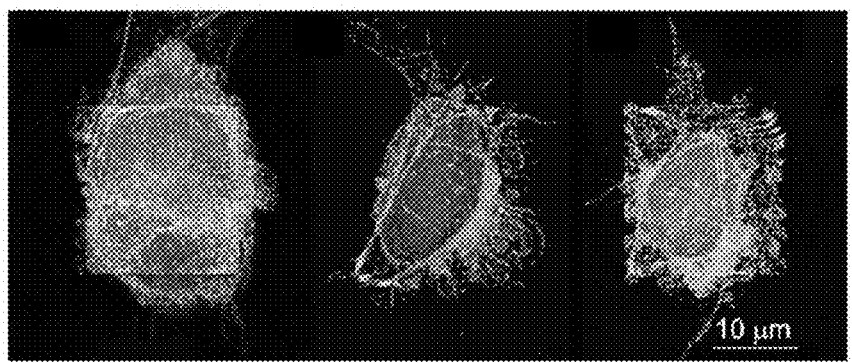
FIGS. 8A-8D are the fluorescent confocal microscopic images of HUVE cells adhered on gold patterns coated with fibronectin (left), REDVY peptide (middle), and KREDVY peptide (right).
Figure 8B:
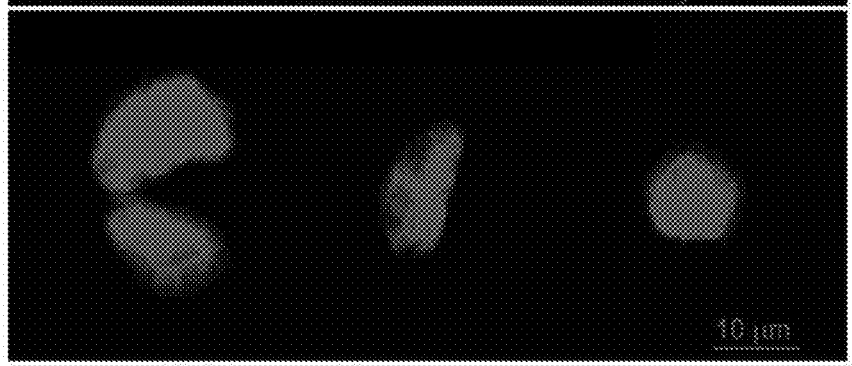
Figure 8C:
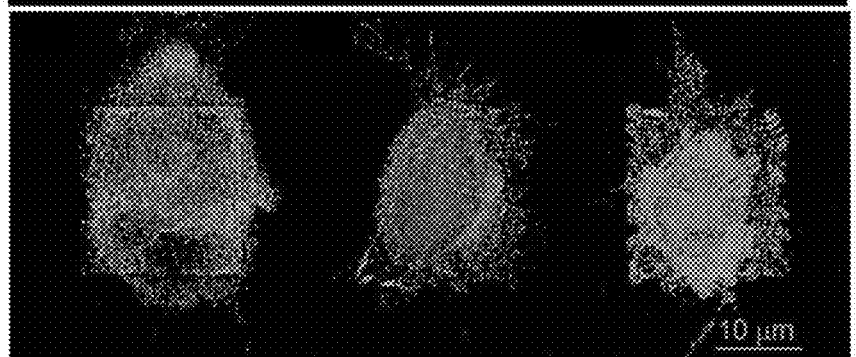
Figure 8D:
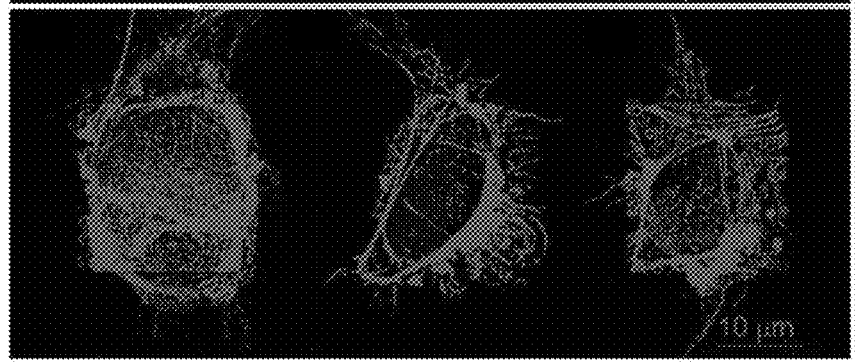
Figures 9A, 9B, 9C, 9D:
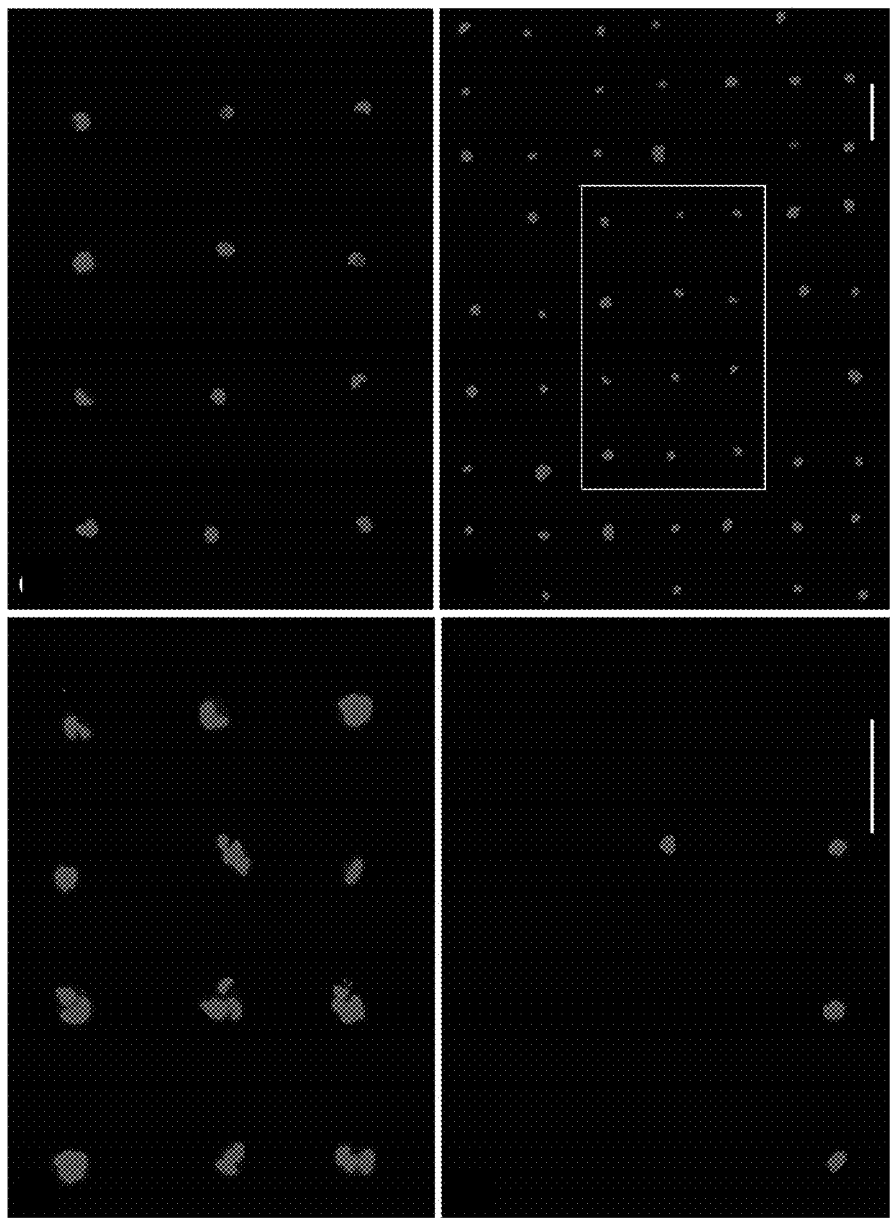
FIGS. 9A-9D are the fluorescence images of HUVE cells cultured on gold-patterned silicon oxide substrates.

The cell adhesion models shown in FIGS. 5A-5C were further validated by cell stain assays. Cells adhered on the substrates were fixed, permeabilized, and stained with DAPI (blue), immunostain containing anti vinculin-FITC (green), ALEXA FLUOR 594 phalloidin dye (red) to reveal the distributions of nuclei, cell-surface focal contacts, and cellular actin filaments, respectively. FIGS. 8A-D show the fluorescence images of cells adhered on the gold squares coated with fibronectin (left), REDVY (middle), and KREDVY (right). FIG. 8A is the overlay of images of FIG. 8B (cell nuclei), FIG. 8C (focal contacts), and FIG. 8D (actin filaments). Cells on the three surfaces generated different morphological, cytoskeletal, and adhesion signals. The nucleus images in FIG. 8B show that two cells were attached on the gold square-based cell adhesion regions with chemically bound fibronectin (left) and single cells on the gold square-based cell adhesion regions with physically adsorbed REDVY (middle) or chemically bound KREDVY (right). FIG. 8C reveals that two cells on the fibronectin modified platform (left) formed fewer focal contacts (per cell) with the substrate than did cells on the KREDVY modified platforms (right), even though many cell binding sequences (hence cell adhesion domains) are available in fibronectin molecules. This supports the hypothesis noted above that only a portion of the available binding sequences in fibronectin participated in binding of a specific cell. The availability of cell binding domains, plus partial coverage of the gold square-based cell adhesion regions by a first-arrival cell, allows for the adherence of a second cell via a different type and/or orientation of binding domains. Spreading of the cells on the fibronectin-modified surface, as shown by the actin filaments (FIG. 8D, left), extended beyond the gold square boundary.

The cell on the REDVY-modified surface has fewer focal contacts with the substrate than the cell on the surface with KREDVY, because the physically adsorbed peptide is prone to detachment from the surface. The cell is not fully spread to cover the entire gold square-based cell adhesion region for the same reason as identified by its actin filament image shown in FIG. 8D, middle. The cell on the KREDVY modified surface formed the densest and most uniform focal contacts with the substrate, and the short peptide molecules confined the cell spreading to the cell adhesion region, as shown in the cell filament image FIG. 8D, right, leaving no additional cell binding domains or space for adhesion of a second cell. The dense KREDVY peptide molecules also facilitate preferential attachment of actin filaments terminated at the edges of cell adhesion region and vinculin proteins concentrated on the domains around cell nucleus and the edges of the cell adhesion region, resulting in a fully spread cellular morphology.

Although covalently bound KREDVY peptides considerably increased the probability of single cell adhesion as compared to protein-mediated cell adhesion, multiple cells were still seen to adhere to individual gold square-based cell adhesion regions on a small number of them. Thus, quantification of single cell coverage is necessary for understanding the capability of this peptide-mediated cell adhesion process. HUVE cells were cultured on fibronectin and peptide modified platforms in standard culture media for 18 hours and stained with DAPI for cell nuclei to emit blue fluorescence. Fluorescence microscopy was used to identify single or multiple cells on gold square-based cell adhesion regions. Cell coverage and single cell population for each type of surface were quantified from 378 gold square-based cell adhesion regions (3 samples×2 areas of interest with 63 cell adhesion regions per area). Cell coverage was calculated from the ratio of gold square-based cell adhesion regions covered with cells to the total number of the cell adhesion regions in the area of interest, and single cell ratio was obtained by dividing the number of gold square-based cell adhesion regions covered with single cells to the total number of cell adhesion regions covered with cells (single or multiple). Exemplary images of adhered cells on three model platforms are shown in FIGS. 9A-D, and quantification results are shown in Table 1. As expected, the fibronectin and KREDVY modified surfaces have higher cell coverage than the REDVY modified surface due to larger number binding domains available on the former two surfaces than on the latter. Both peptide modified surfaces have much higher single cell ratios than the fibronectin modified surface. Clearly, the KREDVY modified surface is the best candidate for single cell patterning in light of both cell coverage and single cell ratio. As a side note, for electrical recording, it is easy to distinguish between single and multiple cells, allowing either type of site to be observed selectively.

TABLE 1

Quantification of HUVEs on gold-patterned silicon substrates modified with fibronectin, REDVY, and KREDVY.

| Surface Coating | % Cell Coverage | % Ratio of single-cell sites/total cell sites |
| --- | --- | --- |
| Fibronectin | 83.47 ± 3.20 | 27.41 ± 3.64 |
| REDVY | 56.28 ± 3.03 | 62.25 ± 3.23 |
| KREDVY | 78.40 ± 3.96 | 72.17 ± 2.49 |

Retaining cell viability after cell adhesion is essential for cell biology studies and biomedical applications such as cell-based sensors and drug screening microarrays. The viability of cells patterned on the three model platforms were studied with an apoptosis assay noted in EXAMPLE section. FIGS. 10A-F show fluorescence images of HUVE cells on cell patterning platforms immobilized with (a) fibronectin, (b) REDVY peptide, and (c) KREDVY peptide after 7 days of cell adhesion. Cells on the platform with chemically bound fibronectin appeared apoptotic and necrotic (FIGS. 10A and 10D). This might be caused by the competitive adhesion of multiple cells on a limited surface area of the gold square-based cell adhesion regions, hindering individual cell growth and survival. This result suggests that large molecule proteins such as fibronectin can result in unpredictable behavior of adhered cells. Because the conformation of fibronectin protein on the gold square-based cell adhesion regions varies from site to site, the degree of interactions of HUVE cells with the binding peptides of the protein and the number of cells attached on each site can differ from pattern to pattern.

No cell necrosis was observed on REDVY and KREDVY modified platforms after 7 days of cell adhesion. However, cells adhered on the physically-adsorbed peptide (REDVY) became apoptotic at day 7. This might be attributable to the detachment of REDVY peptides from the gold surface over time, particularly when the cell culture medium was replenished, which started apoptosis. A similar observation has been reported for anchorage-dependent endothelial cells that undergo apoptosis when detached from extracellular matrix substrates. Cells adhered on the gold based-cell adhesion regions with chemically bound KREDVY remained viable throughout 7 days (i.e., no fluorescence signals), indicating that the covalently bound KREDVY peptide not only facilitates single-cell adhesion through peptide mediated adhesion, but also supports prolonged cell attachment and viability.

It has been reported that a decrease in cell adhesion area would deleteriously restrict cell spreading and that a 20 μm square island coated with fibronectin would lead to cell death. A similar conclusion was reached in that endothelial cells on 20 μm squares coated with fibronectin underwent apoptosis (FIG. 10D). Surprisingly, the surfaces covalently coupled with short peptide molecules on 20 μm squares can promote cell spreading and suppress the apoptosis. This observation suggests that not only the cell adhesion area but also the surface chemistry plays an important role in cellular viability, and a surface bound with adhesive short peptides may help retain cellular viability for a prolonged time.

In another aspect, the present invention provides method for using a cell-patterning array. In one embodiment, the invention provides a method for analyzing a plurality of cells immobilized in an array, including:
  (a) subjecting one or more cells individually immobilized in an array to a stimulus to provide an array comprising individually treated cells, the array comprising a plurality of cell adhesion sites isolated on an inert surface, wherein each cell adhesion site comprises a single cell immobilized thereto by the interaction of one or more ligands attached to the site and one or more cell surface receptors of the immobilized cell, and wherein the inert surface is resistant to cell adhesion;
  (b) individually addressing one or more of the treated cells to measure the effect of the stimulus on the treated cells.

The arrays of the invention can be used in a variety of methods that involve interrogating individual cells (or groups of two or three cells) immobilized at each cell adhesion site. The methods of the invention for analyzing a plurality of cells immobilized in an array can be carried out using any one of the arrays of the invention described herein. It will be appreciated that the methods include arrays having more than one cell immobilized at the cell adhesion site.

In one embodiment, the stimulus is a therapeutic drug compound. The cell-patterning array of the invention can be used in drug screening. For example, the individual cell on each cell adhesion site in the array can be treated with different compounds and the cell response to each compound is measured, therefore, achieving high throughput drug screening by using the cell-patterning array of the invention. Alternatively, the individual cell on each cell adhesion site in the array can be treated with the same compound at different concentrations, therefore, pharmacological and toxicological data of the compound can be obtained.

In another embodiment, the stimulus is a toxin. In this embodiment, the array can be used in toxin detection.

In the method, one or more of the treated cells is individually addressed. The cells in the array can be addressed be any means having the ability to address and interrogate an individual cell. In one embodiment, the treated cells can be addressed optically by measuring the ultraviolet, visible, and infrared adsorption or by measuring the fluorescence or phosphorescence emission. In another embodiment, the treated cell can be addressed by staining with a biological reporting group and then measuring the optical effect of the stained cells. In a further embodiment, the treated cells can be addressed electrically by measuring the capacitance, conductivity, resistivity, or impedance of the treated cells immobilized on the array.

The cell-patterning array of the invention can be used in fields such as biomedical research, diagnostic tools, biosensors, and drug discovery. In one embodiment, the cell-patterning array of the present invention is used in a cell-based biosensor for quick bacterial detection.

An exemplary cell-based biosensor using a cell-patterning array of the present invention was prepared as described in Example 2. Each gold microelectrode was activated with an alkane thiol self-assembly monolayer (SAM) and was covalently reacted with a cell adhesive protein (fibronectin) through an N-hydroxysuccinimide (NHS) coupling agent. The silicon oxide regions were passivated with methoxypolyethylene glycol-silane. In this platform, each microelectrode hosts one to three cells, depending on electrode size and cell concentration in culture.

FIGS. 11A-D show the optical DIC images of macrophage patterned on the gold microelectrodes after 21 hours of cell culture for control cells with no LPS exposure (FIG. 11A) and cells treated with LPS at concentrations of 0.1 μg/mL (FIG. 11B), 1.0 μg/mL (FIG. 11C), and 10 μg/mL (FIG. 11D). The control cells appeared small and round in shape, while LPS-treated cells underwent a morphological change and exhibited an enlarged, dendritic-like shape. This morphological change was likely associated with the synthesis of intracellular peptides and proteins induced by LPS.

Figure 12A:
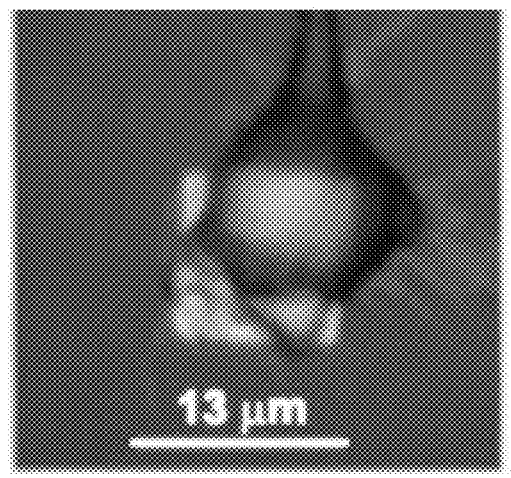
FIGS. 12A, 12C, and 12E are optical DIC images of 100 μm$^2$ electrodes hosting a single macrophage cell, double cells, and triple cells, respectively, after treatment with 1 μg/mL LPS for 21 hours.
Figure 12B:
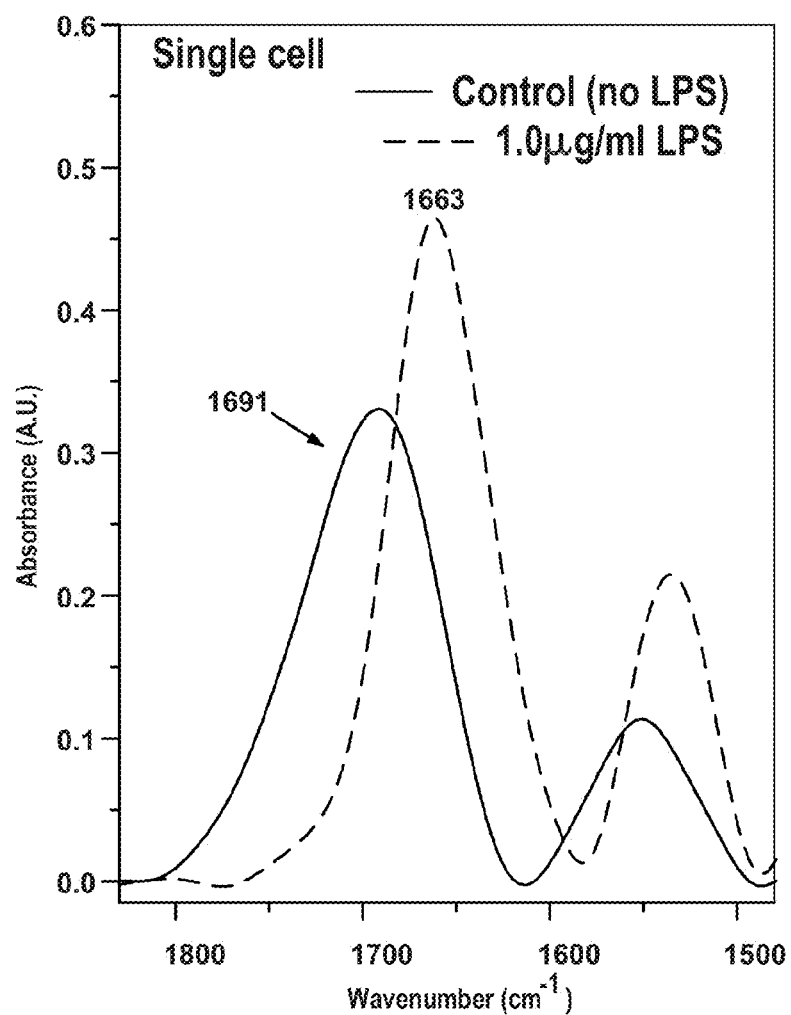
FIGS. 12B, 12D, and 12F are real-time synchrotron IR spectra of a single cell, double cells, and triple cells, respectively, before and after treatment of LPS.
Figure 12C:
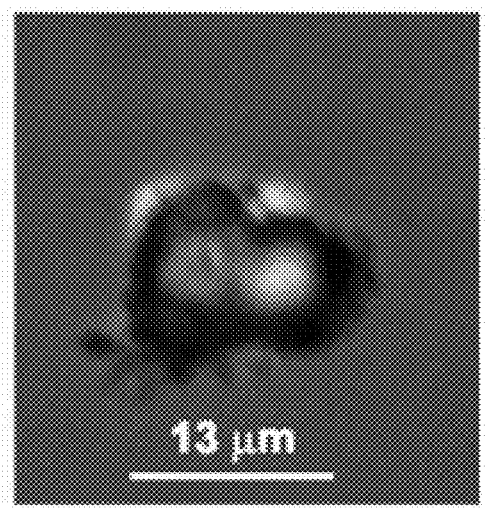
Figure 12D:
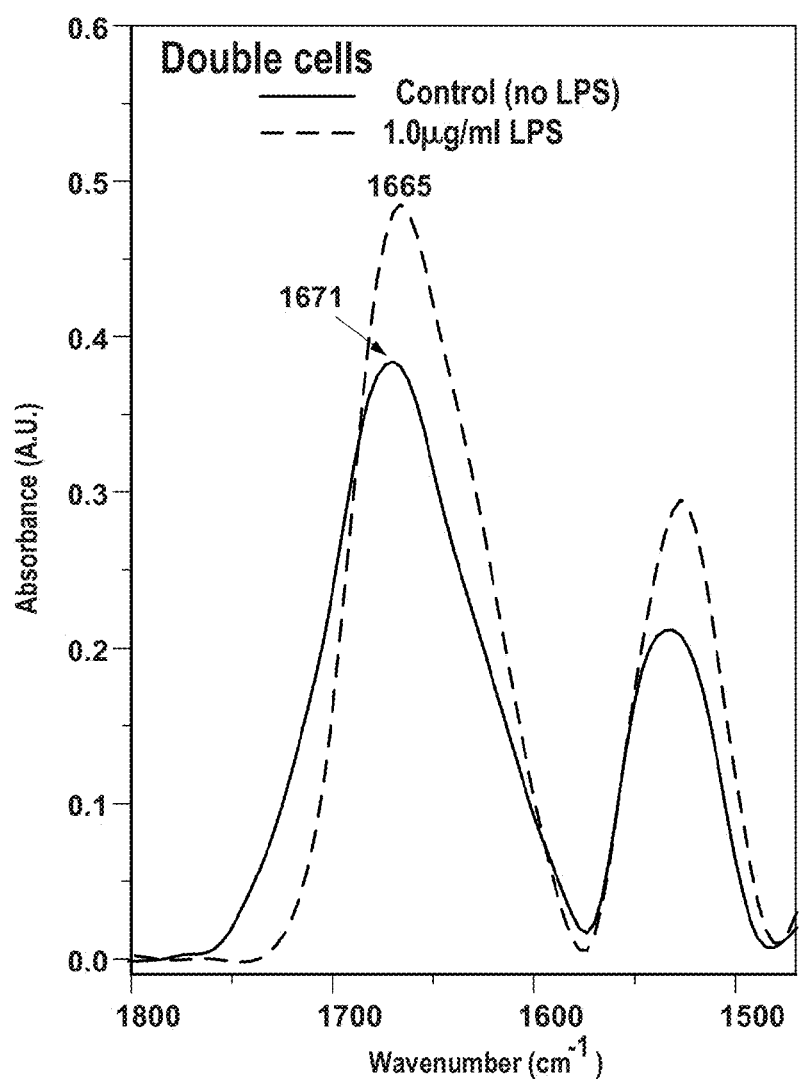
Figure 12E:
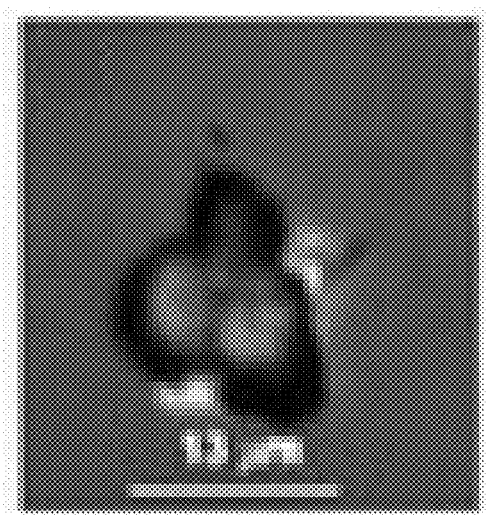
Figure 12F:
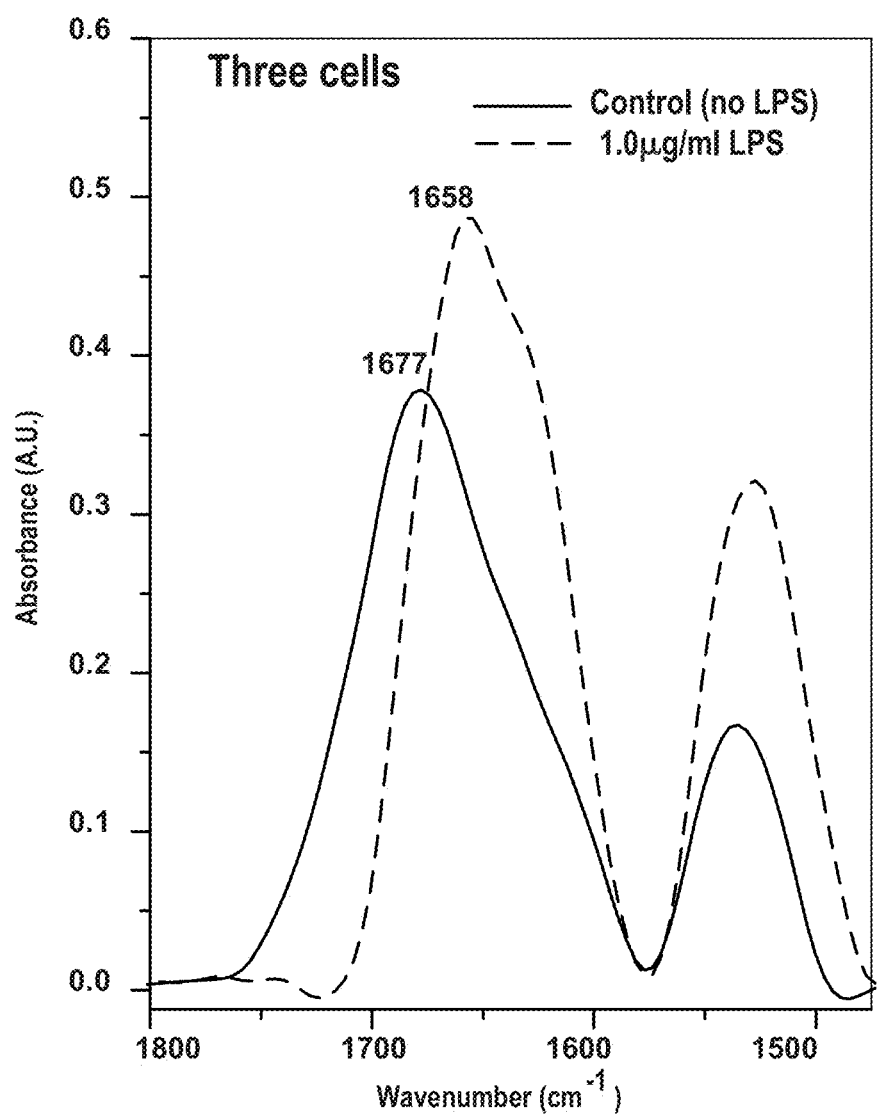

Cells in an isolated state (e.g., one cell on each microelectrode) generally respond differently to an external stimulus than when they are in a communicating state (e.g., a cluster of cells on a microelectrode). To reveal this difference, macrophage cells were patterned in singlet, doublet, or triplet on gold electrodes of 10 μm×10 μm by culturing cells with LPS. FIGS. 12A, 12C, and 12E show exemplary optical DIC images of cell morphology for these cell states, and FIGS. 12B, 12D, and 12F show the corresponding synchrotron IR spectra of the cells before and after exposure to LPS at a concentration of 1 μg/mL for 21 hours.

Table 2 lists the characteristic wave numbers acquired from cells of the three different states before and after exposure to LPS, each averaged over four electrodes of the same state and expressed as mean±S.D. cm$^{-1}$. Prior to exposure to LPS, cells in the singlet state have a characteristic amide I peak at 1691±1.2 cm$^{-1}$, while cells in the doublet and triplet states have the characteristic peaks at 1671±2.5 and 1677±3.2 cm$^{-1}$, respectively.

TABLE 2

Amide I wave number (cm$^{-1}$) of the single, double and triple cells before and after exposure to LPS (1 μg/mL)

| Sample | Single cell | Double cells | Triple cells |
| --- | --- | --- | --- |
| Control Cells | 1691 ± 1.2 | 1671 ± 2.5 | 1677 ± 3.2 |
| LPS-exposed cells | 1661 ± 1.6 | 1665 ± 2.6 | 1658 ± 3.4 |

The difference in amide I characteristic band between the three cell states, even before cells were exposed to LPS, suggests that the cell-cell interactions affect the IR signatures of cells. The degree of IR shifts after the cells were exposed to LPS also differed substantially among the three cell states with the cells in the singlet state exhibiting the greatest shift. Additionally, the cells in the singlet state yielded more consistent data than the other two, as characterized by its smallest standard deviation. The greater uncertainty in IR shifts produced by the cells in doublet and triplet states may be attributable to the interactions between cells in the cell clusters, and furthermore, such uncertainty was seen to increase with increased cell number in the cell cluster.

Figure 13B:
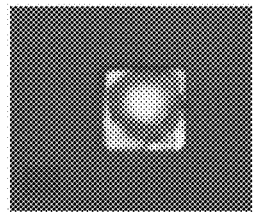
FIGS. 13B-13E are optical DIC images of macrophage cells. Specifically.
Figure 13C:
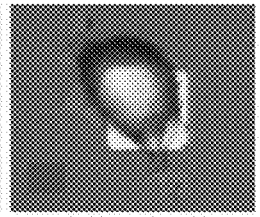
Figure 13D:
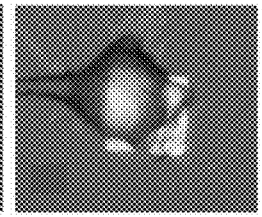
Figure 13E:
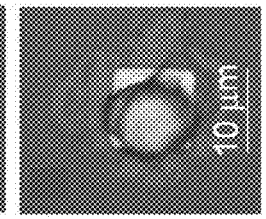
Figure 13A:
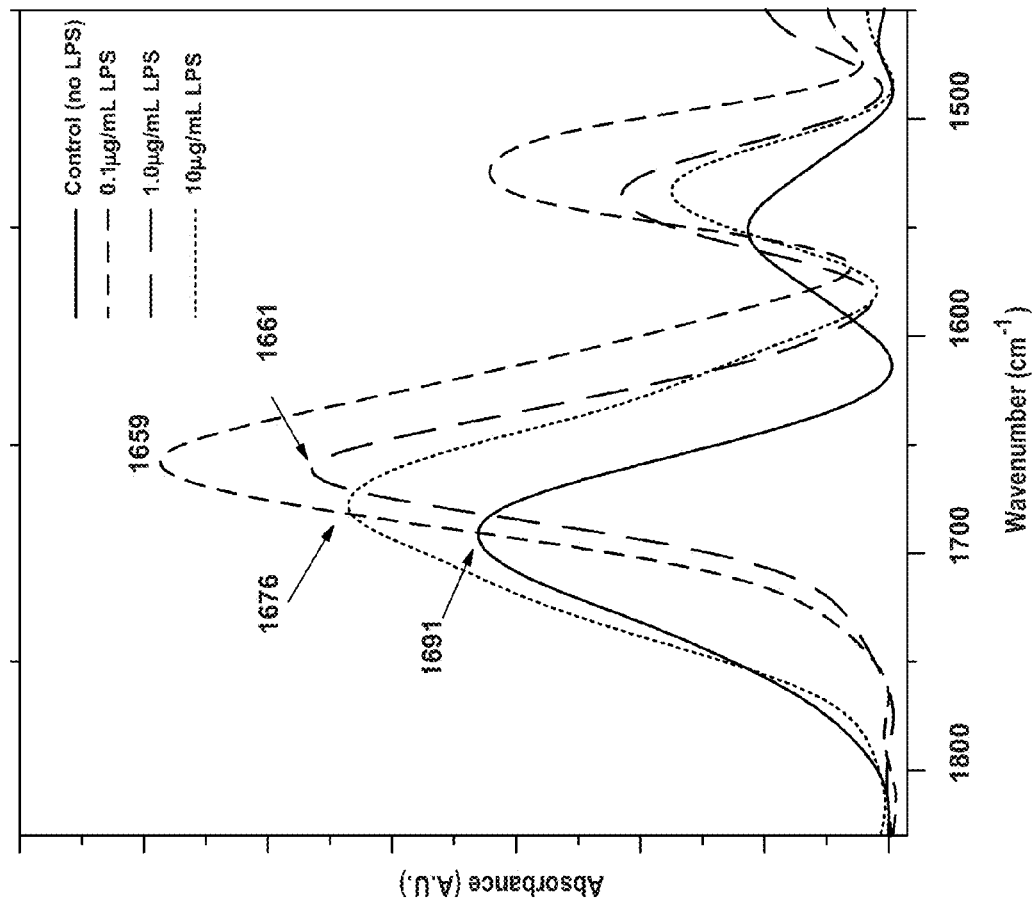
FIG. 13A shows the real-time synchrotron FTIR spectra taken from single macrophage cell patterned on gold electrode with an area of 100 μm$^2$.

FIG. 13A shows the synchrotron IR spectra of macrophage cells in singlet state after treated with LPS at different concentrations for 21 hours. FIGS. 13B-13E show exemplary optical images of the cells from which the spectra were acquired. FIG. 13B corresponds to the cell cultured without PLS (as control), and FIGS. 13C, 13D, and 13E correspond to the cells cultured with LPS at concentrations of 0.1, 1.0, and 10 µg/mL, respectively. Images in FIGS. 13C-13E show that all the LPS-treated cells exhibited dendritic morphology and expanded across the electrode as the LPS concentration increased. The change in IR signature is also dependent on the LPS concentration, characterized by the shifts of both amide I and amide II peaks of cell proteins.

The peak of amide I group (predominantly C=O stretching vibration of amide) shifted from $1691 \pm 1.2$ cm$^{-1}$ before cell exposure to LPS, to $1676 \pm 1.0$ cm$^{-1}$ (10 µg/mL LPS), $1661 \pm 1.0$ cm$^{-1}$ (1 µg/mL LPS), and $1659 \pm 1.7$ cm$^{-1}$ (0.1 µg/mL LPS) post-exposure. These peak shifts in wave number are presented as main±standard deviation calculated from eight electrodes of two substrates for each sample set. The characteristic peaks moved towards lower wave numbers initially with increased LPS concentration, but to higher wave numbers after reaching a minimum at LPS concentrations between 0.1 and 1.0 µg/mL. This peak reversion is believed to be due to cell death at high LPS concentrations.

Figure 14B:
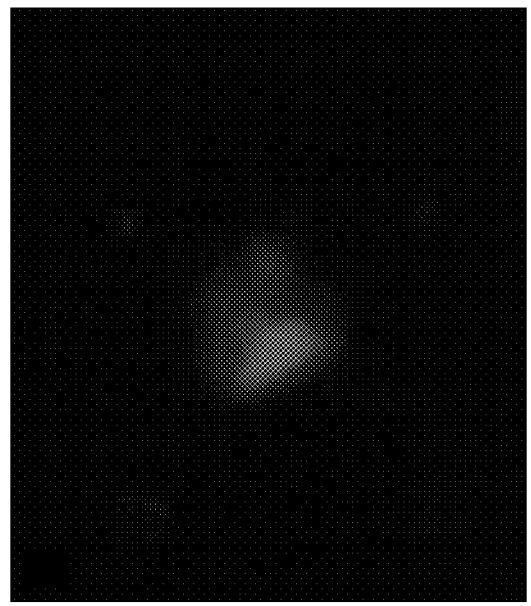
FIGS. 14A and 14B are optical DIC images of a single macrophage cell patterned on a gold electrode with a surface area of 100 μm$^2$, cultured with 10 μg/mL LPS for 21 hours, and stained.
Figure 14A:
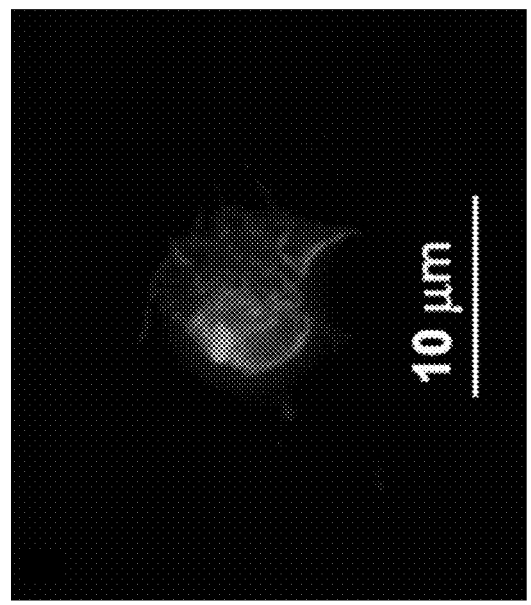

To confirm this hypothesis, cellular viability was assessed by staining cells in singlet state with Annexin V (green for apoptotic cells) and propidium iodide (red for necrotic cells) after they were exposed to LPS at concentrations of 0.1, 1.0, and 10 µg/mL, respectively. FIGS. 14A and 14B show exemplary images of cells treated with LPS at a concentration of 10 µg/mL, indicating that the cell underwent apoptosis and necrosis. Cellular viability was quantified in terms of ratios of apoptotic and necrotic cells to the total cells on 238 electrodes on duplicate substrates. The result indicated that cells treated with LPS at a concentration of 10 µg/mL underwent 66.5% apoptosis (positive Annexin V staining) and 41.1% necrosis (positive propidium iodide staining), respectively. Control cells and the cells treated with LPS at concentrations of 0.1 and 1.0 µg/mL showed less than 8% apoptosis and no necrosis was identified. Images of cells treated with LPS at 0.1 and 1.0 µg/mL are not shown in the figure due to absence of statistically significant fluorescence.

These experiments showed a LPS concentration-dependent response of single cells that can be readily detected by FTIR. It is worthwhile to note that a peak shift of 2-7 cm$^{-1}$ in wave number has been used to identify diseased tissue from healthy tissues in multi-cell platforms. Here, a shift in the order of a few tens of wave numbers (e.g., 30 cm$^{-1}$ observed at LPS concentration of 1.0 µg/mL) demonstrated a high sensitivity of this single-cell-based platform. Such sensitivity may allow for identification of bacterium of very small concentration and sample volume. Furthermore, the degree of bacterium invasion (e.g., the percent of macrophage cells infected by LPS) can be assessed over a large number of sensing electrodes, and heterogeneous cellular behavior can be investigated with such a microarray of macrophages.

Figure 15A:
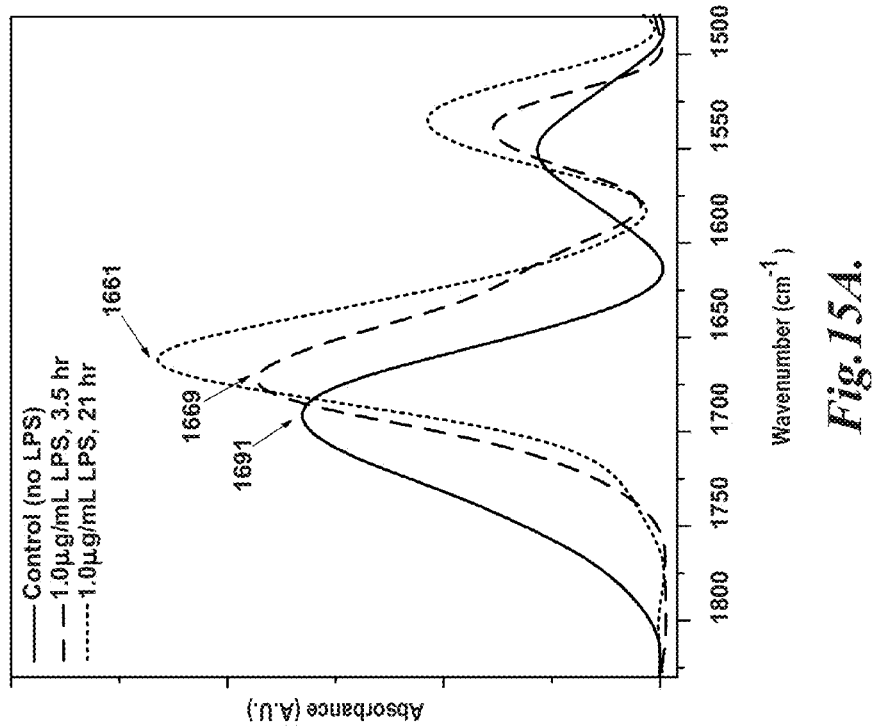
FIG. 15A shows the real-time synchrotron IR spectrum of a single cell response to LPS (1.0 μg/mL) over time.
Figure 15B:
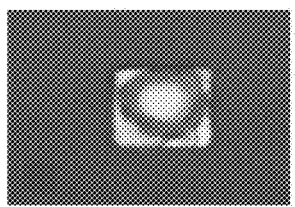
FIGS. 15B, 15C, and 15D are optical DIC images of a single macrophage cell with no LPS treatment, with LPS (1.0 μg/mL) treatment for 3.5 hours, and with LPS (1.0 μg/mL) treatment for 21 hours, respectively.
Figure 15C:
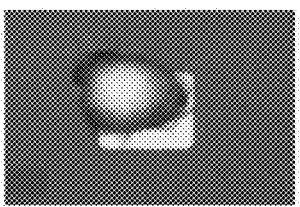
Figure 15D:
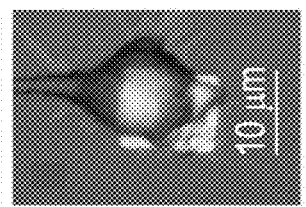

FIG. 15A shows IR spectra acquired by synchrotron-based FTIR microspectroscopy from single cells patterned on an array of gold microelectrodes before exposure to LPS as well as post-exposure to LPS at a concentration of 1 µg/mL for 3.5 and 21 hours. The optical images in FIGS. 15B, 15C, and 15D show the corresponding cell morphology of the single macrophage cells on gold electrodes with a size of 100 µm$^2$ over the same time course. The morphology of the LPS-treated cell was seen to change with LPS exposure time, from a spherical shape to a dendritic shape with increased size over time. The change in IR spectrum over time during the LPS exposure is characterized by the continued shifts of both amide I and amide II peaks from high to low wave numbers and an increase in signal intensity. The IR shifts in amide I spectrum may indicate the change in protein structure as a result of upregulating various proteins and peptides involved in the macrophage activation cascade initiated by LPS. It has been reported that LPS induced the synthesis of various polypeptides within macrophage cells. Some peptides were short-lived (did not accumulate in LPS-treated cells) and played a regulatory role while others were long-lived (accumulated in LPS-treated cells) and played a functional role. Not wanting to be limited by the theory, the IR shift and the intensity increase for cells exposed to LPS for 3.5 hours might be due to synthesis of short-lived peptides. The IR peak change for cells treated with LPS for 21 hours might be attributable to the presence of long-lived polypeptides. The presence of a single peak for all the amide I bands in FIG. 15A suggests that proteins with α-helical secondary structure are dominant. The current experiment suggests that the variation in wave number in response to LPS invasion, as detected by the single-cell system described here, is adequate for identification of bacterium in a short period (hours here versus days by conventional bacterial detection methods).

IR signal intensity depends directly on the brightness of IR source and the size of the electrode that hosts the cell. In a gold-patterned silicon platform, the maximum signal intensity is obtained when the synchrotron IR focal point is at the center of the gold electrode and the noise from the silicon oxide background is minimized. The superior brightness of the synchrotron source with a spatial resolution less than 10 µm provides high sensitivity for detection of single cells on electrodes of 100 µm$^2$ as shown above. However, a conventional IR thermal source with an effective beam diameter of about 75 µm requires electrodes larger than the beam size to reduce the signal loss to the surrounding area. To study the effect of electrode size on detection sensitivity and the possible use of conventional FTIR for bacterial detection with our single-cell system, FTIR spectra from single-cell arrays with electrode sizes of 25, 100, and 400 µm$^2$, respectively, were acquired using both synchrotron and conventional FTIR spectromicroscopy.

Figures 16A, 16B:
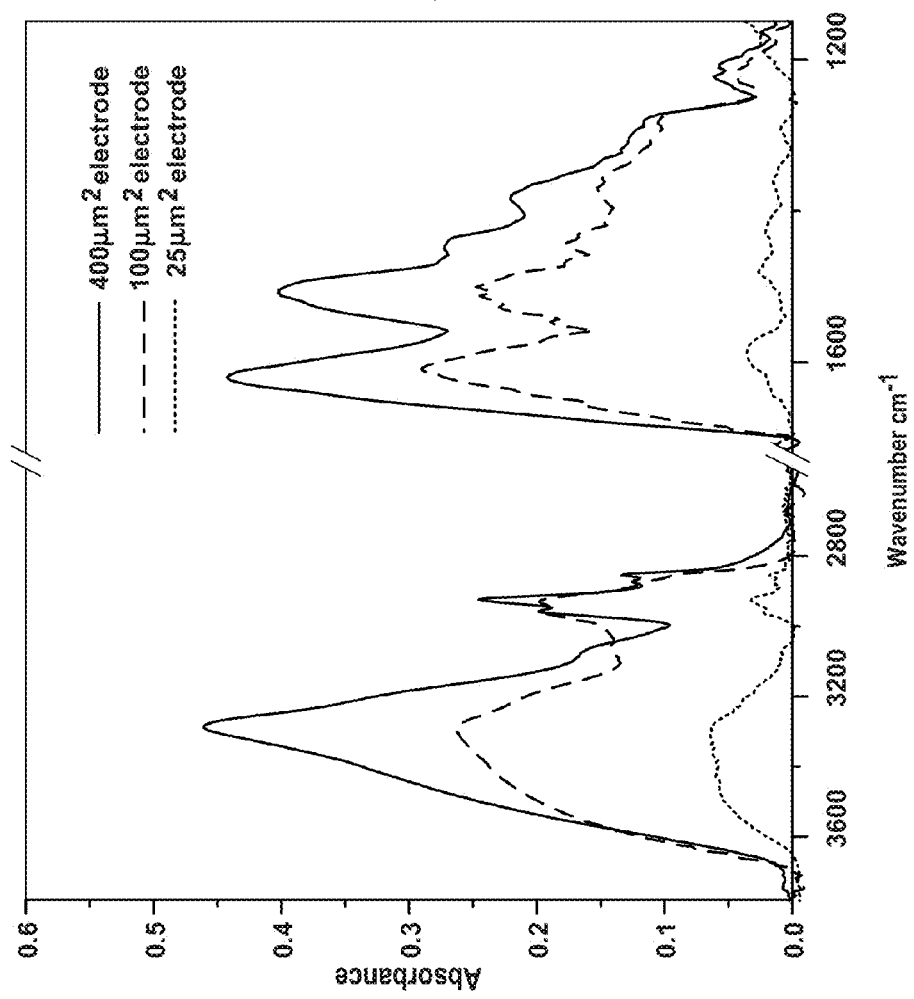
FIGS. 16A-16D compares FTIR spectra of single macrophage cells on electrode of three different sizes: 25 μm$^2$, 100 μm$^2$, and 400 μm$^2$.
Figures 16C, 16D:
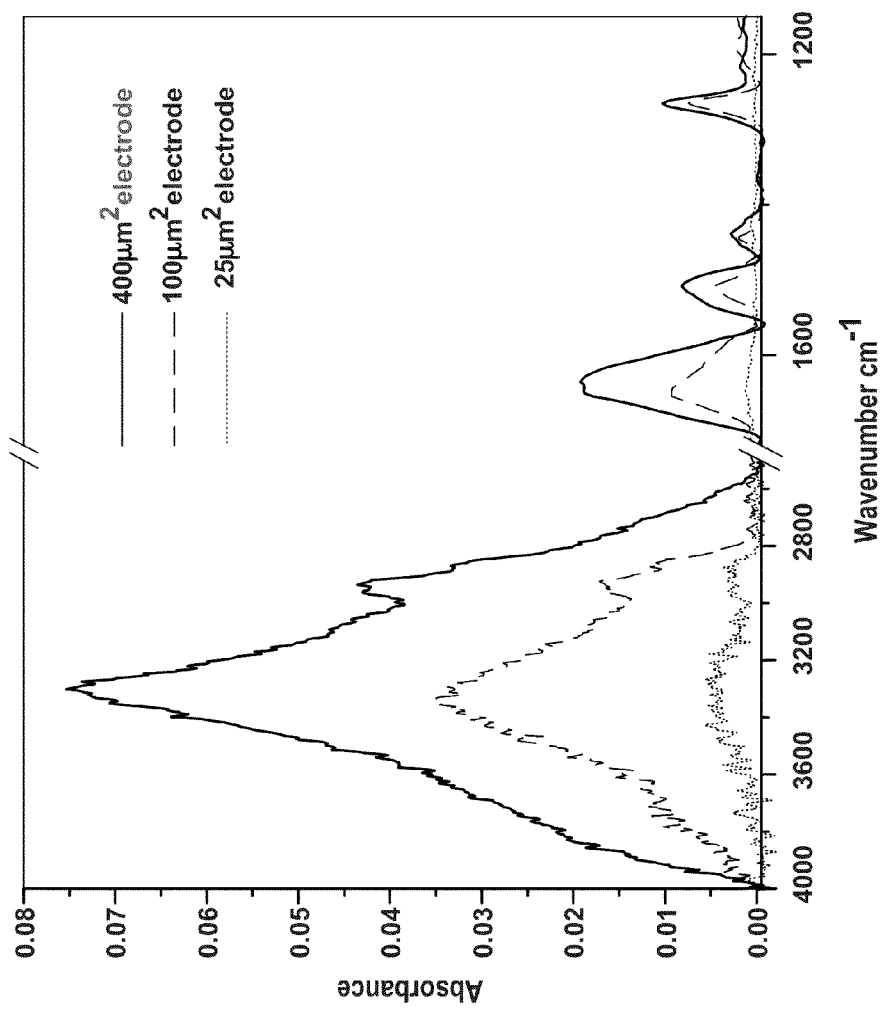

FTIR spectra shown in FIGS. 16A and 16B were acquired by synchrotron FTIR. FTIR spectra shown in FIGS. 16C and 16D were acquired by conventional FTIR. The signal intensity was seen to increase with increased electrode size for both systems. Characteristic peaks of cell membranes at wave numbers of 2800-3600 cm$^{-1}$ and cellular proteins at 1200-1700 cm$^{-1}$ are resolved well with the synchrotron source even for the smallest electrode size (25 µm$^2$) (FIGS. 16A and 16B). Though at a significantly lower signal intensity, the IR signals acquired with the conventional FTIR are well resolved for the 100 and 400 µm$^2$ microelectrodes (FIGS. 16C and 16D). These results indicate that the current single-cell platform can be used with conventional FTIR spectromicroscopy if the electrode surface area is larger than 100 µm². It is noteworthy mentioning that although increasing electrode size will increase the signal intensity, it also increases the probability of adhesion of multiple cells on an electrode, rendering single-cell patterning more difficult. A comparison of the IR spectra acquired from cells on gold electrodes of different sizes reveals no identifiable difference in IR signature.

In a related aspect, the invention provides systems for analyzing a plurality of cells immobilized in an array. The system includes one or more arrays of the invention having one or more cells immobilized on the arrays' cell adhesion sites, and an analytical instrument capable of individually addressing and interrogating the immobilized cells. Representative analytical instruments include optical instruments (e.g., infrared spectrometers, fluorescence spectrometers) and electrical instruments that measure capacitance, conductance, resistivity, impedance).

In another aspect, the present invention provides arrays having a passivated silicon oxide surface. In this aspect, arrays are provided that have improved surface characteristics that provide inert surfaces having increased stability thereby enhancing their cell resistance capacity and the lifetime and effectiveness of the arrays.

In one embodiment, the array having a passivated silicon oxide surface for guided cell patterning includes a plurality of individually immobilized cells at defined cell adhesion sites isolated on an inert surface resistant to cell adhesion. For these arrays, the cell adhesion sites are prepared as described above for the arrays of the invention in which their silicon substrate surfaces are not treated as described below. In this embodiment, the inert surface is a passivated silicon oxide surface that has been prepared by first depleting native oxide from the silicon surface and then oxidizing the native oxide depleted surface. The inert surface is resistant to cell adhesion by covalently coupling polyalkylene oxides to the silicon oxide surface.

In one embodiment, the silicon oxide surface has about 40% to 65% by weight Si, from about 5% to about 20% by weight $SiO_{x<2}$, and from about 20% to about 40% by weight $SiO_2$. In another embodiment, the silicon oxide surface has from about 50% to 60% by weight Si, from about 10% to about 15% by weight $SiO_{x<2}$, and from about 25% to about 35% by weight $SiO_2$. In a further embodiment, the silicon oxide surface has about 58% by weight Si, about 12% by weight $SiO_{x<2}$, and about 30% by weight $SiO_2$.

These arrays having passivated silicon oxide surfaces are prepared by a method that includes:
(a) providing a metal-patterned silicon substrate having an array of metal surfaces disposed on a silicon surface;
(b) exposing the substrate to an oxide etch to remove native oxide from the silicon surface to provide a native oxide depleted silicon surface;
(c) oxidizing the native oxide depleted silicon surface with an oxidizing agent to provide a silicon oxide surface; and
(d) passivating the silicon oxide surface by covalently coupling polyalkylene oxide moieties to the silicon oxide surface to provide a surface resistant to cell adhesion isolating each metal surface of the metal surface array.

In one embodiment, the method further comprises forming a self-assembly monolayer on each metal surface to provide an array of monolayers disposed on the silicon oxide surface. In one embodiment, the method further comprises attaching a plurality of ligands to each self-assembly monolayer to provide an array of cell adhesion sites. In one embodiment, the method further comprises immobilizing one or more cells at each cell adhesion site through the interaction of the ligands and one or more cell surface receptors of the cells. These additional steps can be carried out as described above for the other arrays of the invention.

In the method, exposing the silicon substrate to an oxide etch to remove native oxide from the silicon surface to provide a native oxide depleted silicon surface and oxidizing the native oxide depleted silicon surface with an oxidizing agent to provide a silicon oxide surface, leads to the unique $Si/SiO_{x<2}/SiO_2$ composition noted above for the array having a passivated silicon oxide surface.

Native oxide on the silicon surface can be removed by any useful technique that is effective in removing the native oxide to provide a native oxide depleted silicon surface. Representative oxide etches include a mixture of hydrogen fluoride (HF) and ammonium fluoride ($NH_4F$), Piranha (HF/$NH_4F$ 5:1 v/v), and NANOSTRIP ($H_2SO_5$).

The native oxide depleted silicon surface can be oxidized by any suitable oxidizing agent to afford a silicon oxide surface. Representative oxidizing agents include dry oxygen, ozone, hydrogen peroxide, and chromic acid.

In one embodiment, the native oxide depleted silicon surface is oxidized with dry oxygen at an elevated temperature to provide a silicon oxide surface with a dry thermally grown oxide layer. In one embodiment, the native oxide depleted silicon surface is oxidized with dry oxygen at from about 300° C. to about 500° C. for from about 5 to about 24 hours to provide a silicon oxide surface. A representative silicon oxide surface with dry thermally grown oxide can be obtained by exposing the surface to buffered oxide etch (HF/$NH_4F$ 5:1 v/v) for 60 seconds to remove native oxide on the surface, rinsing with deionized water to remove the native oxide on silicon regions, and flushing the treated surface with a dry oxygen flow for 6 hours at 400° C. to provide an oxide surface with a 60 Å oxide layer on the surface.

In one embodiment, the native oxide depleted silicon surface is oxidized with wet oxygen at an elevated temperature to provide a silicon oxide surface with a wet thermally grown oxide layer. A representative silicon surface with wet thermally grown oxide can be obtained by exposing the surface to buffered oxide etch (HF/$NH_4F$ 5:1 v/v) for 60 seconds, rinsing the surface with deionized water to remove the native oxide to provide a treated surface, and flushing the treated surface with a wet oxygen flow at 850° C. to provide an oxide surface with a 1,000 Å oxide layer on the surface.

The thickness of the oxide layer can vary according to oxidation condition. In general, the thickness of the oxide layer can be from about 30 Å to about 1,500 Å depending upon the condition of the oxidation reaction. In one embodiment, the thickness of the oxide layer is about 60 Å. In another embodiment, the thickness of the oxide layer is about 1,000 Å. In one embodiment, the silicon oxide surface comprises an oxide layer having a thickness of from about 50 Å to about 1500 Å. In another embodiment, the silicon oxide surface comprises an oxide layer having a thickness of about 60 Å. In one embodiment, the silicon oxide surface comprises an oxide layer having a thickness of about 1000 Å.

Several arrays for cell-patterning have been prepared and their cell-patterning capabilities were compared, as described in Example 3. Three types of surfaces that contained native oxide, dry thermally grown oxide, and wet thermally grown oxide, respectively, were produced as a basis for the inert surface. As used herein, "silicon surface with native oxide" refers to a silicon surface without any chemical modification. The cell-patterning platform based on a silicon surface with native oxide was used as a comparison for evaluating the effectiveness of the cell-patterning platforms of the present invention having a passivated silicon oxide surface.

Silicon substrates were cleaned with piranha (hydrogen peroxide/sulfuric acid 2:5 v/v) at 120° C. for 10 minutes, dipped in HF and rinsed with DI water thoroughly. A layer of positive photoresist was then coated on the surface and an array of gold square was patterned on the silicon oxide substrate by conventional microfabrication. Specifically, a layer of titanium (Ti) was deposited onto photoresist-developed substrates. A gold film was subsequently deposited onto the titanium. The photoresist was dissolved and the remaining metal film was lifted off.

The surface with native oxide was formed as a result of exposure of the substrates to the air. The surface with dry oxide was created by additionally exposing the surface to buffered oxide etch (HF/NH$_4$F 5:1 v/v) for 60 s and rinsing with DI water to remove the native oxide on silicon regions, followed by flushing with a dry oxygen flow for 6 h at 400° C., yielding a 60 Å oxide layer on the silicon regions. The surface with wet oxide was prepared following the same procedure except that the substrates were placed under a wet oxygen flow at 850° C., yielding a 1000 Å oxide layer on the silicon regions.

The gold-patterned substrates were then modified. The silicon regions with native, dry, or wet oxide were reacted with a low molecular weight M-PEG-silane (molecular weight=460-590 Dalton) to form inert (i.e., non-cell adhesive) regions. The gold regions were first reacted with COOH-terminated alkyl thiols to form a COOH-terminated SAM containing a plurality of COOH groups, followed by covalently bonding proteins to at least a portion of COOH groups to form cell adhesive regions.

High-resolution XPS spectra were acquired on the solid silicon substrates before and after surface modification with methoxy-PEG-silane (M-PEG). The results were shown in FIGS. 2A-2H. The native oxide substrate showed the expected binding energy of elemental silicon (about 99.7 eV) and SiO$_2$ (about 103.5 eV). The dry oxide surface showed a similar spectrum as that of native oxide but with an asymmetric peak at about 102 eV, indicating the presence of a different silicon oxide state than those present on the native and wet oxide surfaces. This additional oxide state corresponds to silicon oxidation states (SiO$_{x<2}$) other than SiO$_2$. The wet silicon oxide surface had only a SiO$_2$ peak in its XPS spectrum indicating that the silicon background was completely covered by silicon dioxide.

Survey spectra indicated an increase in the carbon content and a decrease in the silicon content on all of the PEG-modified surfaces compared to that of their unmodified counterparts. More oxygen was observed on both native and dry oxide after PEG modification, as opposed to wet oxide surfaces. The decreased amount of oxygen on the wet oxide was due to the fact that the wet oxide surface was mainly composed of silicon dioxide before PEG modification.

Table 3 represents the high-resolution XPS analyses of the Si$_{2p}$ components on the oxide surfaces and the C$_{1s}$ components on the PEG-modified surfaces. The spectra of high-resolution C$_{1s}$ for all PEG-modified surfaces appeared to be similar, and the amounts of PEG on them were about the same. Further elaborations on the PEG component analysis are presented in the following sections.

TABLE 3

High resolution XPS Si$_{2p}$ and C$_{1s}$ analyses[a]

| (A) sample | % composition | | | (B) sample | % composition | | |
|---|---|---|---|---|---|---|---|
| | Si | SiO$_{x<2}$ | SiO$_2$ | | C—H | C—O | C=O |
| native oxide | 69.64 | | 30.36 | native oxide | 15.1 | 80.6 | 4.3 |
| dry oxide | 58.45 | 11.85 | 29.7 | dry oxide | 14.8 | 82 | 3.2 |
| wet oxide | | | 100 | wet oxide | 15 | 79.7 | 5.3 |

[a]Spectra were taken at a 55° takeoff angle from
(A) silicon oxide substrates and
(B) PEG-modified silicon oxide substrates.
The percentages are atomic percents of each type of surface atom calculated from survey spectra scan (FIGS. 2A-2H).

Water contact angles on all three types of silicon surfaces were measured after the surfaces were modified with PEG. The contact angle values of the three surfaces are 31.6±1.34° for native oxide; 29.8±0.83° for dry oxide; 30.4±2.4° for wet oxide.

Despite the apparent differences in the nature of silicon oxide layers grown on the three surfaces before M-PEG-silane modification, both the contact angle measurements and XPS data indicated that about the same amount of PEG was coated on all three surfaces.

Protein adsorption on the gold-patterned surfaces was visualized with fluorescence microscopy on unmodified (clean Au/SiO$_2$) surfaces and on the cell-patterning platform having the cell-adhesive regions comprising alkyl SAM on gold and the inert regions with PEG on silicon oxide as show in FIG. 1B. The platform was exposed to fibronectin-Cy3 conjugate immediately following the surface modification. FIGS. 3A-F show fluorescent images of the unmodified (left panel) and modified (right panel) surfaces with the silicon background immobilized with native oxide (FIGS. 3A and 3B), wet oxide (FIGS. 3C and 3D), and dry oxide (FIGS. 3E and 3F).

For the unmodified surfaces, proteins were randomly adsorbed over both the Au and silicon oxide regions (FIGS. 3A, 3C, and 3E), and particularly, the surface with wet oxide was heavily covered with proteins with no electrodes visible. The results reveal the influence of the silicon oxide state on protein adsorption. After surface modification, the protein was selectively adsorbed on gold electrodes of all three surfaces (FIGS. 3B, 3D, and 3F). However, a slight nonspecifically adsorbed protein was seen on the silicon region of the wet oxide surface (FIG. 3D). This phenomenon can be attributed to the strong affinity of the wet oxide for protein adsorption (FIG. 3C). This high affinity makes the wet oxide surface more susceptible to the defects presented in the PEG coating in preventing protein adsorption than the other surfaces, resulting in a high local protein adsorption (and subsequent cell adhesion when exposed to cells) on defected sites.

The PEG-modified dry oxide surface showed high protein resistance. Quantitative measurements of fluorescence intensities of the silicon surfaces yielded the following: wet oxide, 60; native oxide, 17; and dry oxide, 11, from the unmodified surfaces. This indicates that the dry oxide layer on the silicon region is the least biofouling layer by itself, and thus, the order of possible biofouling appeared to be: dry oxide<native oxide<wet oxide.

Cell selectivity was studied by culturing murine macrophage cells on the cell-patterning platform and monitored for up to 10 days, which is a typical time period for practical applications of cell-based biosensors. Cell selectivity was defined as selective confinement of cells to the designated regions— the gold-based cell-adhesive regions in the present invention. Macrophage was used as the model cell line for cell selectivity study because of its important physiological functions in the human body. For example, they have potentials for use as cellular delivery vehicles for gene therapy of diseased tissues and are an important source of mitogenic growth factors and proangiogenic cytokines in wound healing. Selective suppression of macrophage activation is also a possible approach to diminishing local inflammation. Combined with ink jet or other analyte-positioning techniques, surfaces patterned with macrophages may be used as sensing arrays for rapid detection of a variety of external stimuli and screening of drugs.

DIC reflective images were acquired after 2 days of cell culture and up to 10 days because all of the surfaces had formed a uniform and highly selective cell pattern up to 1 day during which time no apparent difference on cell morphology was observed. These results are shown in FIGS. 4A-4I. Images were acquired on day 3, 7, and 10 (presented horizontally from left to right over time). FIGS. 4A-4C, 4D-4F, and 4G-4I are the substrates with native oxide, wet oxide, and dry oxide, respectively.

It is noted that the cell selectivity over time differed dramatically among the three patterned platforms. Cells started to migrate to the inert regions on the native oxide surface on day 3 (FIG. 4A), and the patterned surface completely lost cell selectivity on day 10 (FIG. 4C). The cell-patterning platform with wet oxide-based inert regions (FIGS. 4D-4F) has much better cell selectivity than the platform with native oxide-based inert region. The platform with dry oxide-based inert regions shows very high cell selectivity through the duration of the study (10 days) as shown in FIGS. 4G-4I. Dry oxide has an additional advantage of being a better insulator, which would enhance the performance of cell-based biosensors by increasing the electrical signal-to-noise ratio.

Not wanting to be bound by the theory, it is noted that the prolonged cell selectivity on the platform with dry oxide-based inert regions might be related to the intermediate oxidation state for the silicon (Table 3 A). This is a more chemically reactive state than a fully stable $SiO_2$ and may result in different types of reactions. It has been reported that methyl trimethoxy silanes react directly with dehydroxylated silica surfaces to form stable, chemically bound alkylsiloxanes and alkoxides at 300 K and that model silane coupling agents can react directly with the highly strained siloxane bonds present on dehydroxylated silica without the involvement of surface hydroxyl groups. In addition, it has been shown that trimethoxy silanes that are strongly bonded on surfaces at 330 K are extremely thermally stable. The fact that the PEG used for this study was a trimethoxy silane-PEG and was reacted with the surface at about 333 K may justify the observed behavior of the dry oxide surface. Thus, the interaction of PEG with the active state of silicon oxide might have contributed to formation of a more stable PEG coating on the silicon substrate.

To validate this theory, the stabilities of the PEG coatings on three model surfaces under cell culture condition were assayed using serum-containing medium. PEG-modified surfaces were incubated in the medium at 37° C. and 5% humidity, and XPS analysis was performed on the samples on day 0, 3, 7, and 10. The results are shown in Table 4.

respectively. A high $\Delta CO/CO_0$ value corresponds to a high degradation rate. The results calculated from data in Table 4 are shown in Table 5.

TABLE 5

Time-dependent degradation of the PEG coatings in cell culture medium at 37° C. and 5% humidity.

| | degradation rate $(CO_0 - CO_t)/CO_0$ | | |
|---|---|---|---|
| sample | PEG-native | PEG-dry | PEG-wet |
| day 3 | 0.719 | 0.036 | 0.035 |
| day 7 | 0.723 | 0.047 | 0.096 |
| day 10 | 0.728 | 0.259 | 0.422 |

PEG on the native oxide-based inert region showed a considerable degradation on day 3 ($\Delta CO/CO_0=0.719$). The PEG degradation proceeded much slower on the dry oxide and wet oxide-based inert regions ($\Delta CO/CO_0=0.036$ and 0.035, respectively). PEG on the both types of inert regions remained stable up to 7 days and was partially degraded afterward. PEG on dry oxide had the least degradation for up to 10 days. When this result is compared with the cell-patterning images shown in FIGS. 4A-I, a marked consistency is seen: the cell selectivity over time is directly correlated to PEG degradability.

Not wanting to be limited by the theory, it is believed that a stable PEG coating is essential to achieving improved cell selectivity and that the prolonged PEG integrity in cell cultural medium may be related to the presence of oxide states other than silicon substrates. Such an oxide surface might have served a dual function purpose: a relatively low affinity to proteins that suppress the protein adsorption in a surface with favorable chemistry on which a stable PEG coating can be developed. The silicon substrate with trioxide achieves a more stable PEG coating than the silicon surfaces with native or wet oxide that are typically used in development of bio-MEMS devices.

Thus, maintaining PEG integrity over time, particularly in cell culture medium, as far as ligand-mediated cell patterning

TABLE 4

High resolution XPS C1s analysis of PEG-modified substrates[a]

| | % composition | | | | | | | | | | | |
|---|---|---|---|---|---|---|---|---|---|---|---|---|
| | day 0 | | | day 3 | | | day 7 | | | day 10 | | |
| sample | C—H ~285 | C—O ~287 | C=O ~288 | C—H ~285 | C—O ~287 | O—C=O ~289 | C—H ~285 | C—O ~287 | O—C=O ~289 | C—H ~285 | C—O ~287 | O—C=O ~289 |
| PEG-native | 15.1 | 80.6 | 4.3 | 72.0 | 22.6 | 5.4 | 72.7 | 22.3 | 5 | 70.8 | 21.90 | 7.3 |
| PEG-dry | 14.8 | 82 | 3.2 | 19.1 | 79.0 | 1.9 | 20.1 | 78.1 | 1.8 | 37 | 60.7 | 2.3 |
| PEG-wet | 15 | 79.7 | 5.3 | 17.9 | 76.9 | 5.2 | 22.3 | 72 | 5.7 | 49.8 | 46 | 4.2 |

[a]Spectra were taken at a 55° takeoff angle, after the substrates were incubated in cell culture medium for 3, 7, and 10 days.

Most noticeable is the appearance of the O—C=O peak at about 289 eV on all the platforms after 3 days of cell culture. This can be attributed to the partial oxidation of PEG in the cell culture medium. The amount of O—C=O was maximum on the native and wet oxide-based inert regions and minimum on the dry oxide-based inert regions through the period of study. The change in this peak provides an indication of the PEG oxidation level over time but does not rule out the possibility of PEG decomposition or degradation. PEG degradation can be estimated by the change in the amount of C—O over time. In this context, the degradation rate is defined as $\Delta CO_t/CO_0=(CO_0-CO_t)/CO_0$, where $CO_0$ and $CO_t$ represent the amount of C—O initially and at time t, is concerned, is a key to the success of prolonged cell selectivity and biostability. This was achieved by the present invention by engineering the silicon surface to change its native oxidation state, on which a more stable PEG coating can be obtained.

The following examples are provided for the purpose of illustrating, not limiting, the invention.

EXAMPLES

Materials

The following materials and chemicals were used as received: NANOSTRIP 2× (Cyantek, Fremont, Calif.), 2-[methoxy(polyethyleneoxy)propyl]trimethoxysilane ($M_w$=460-590 Da) (Gelest, Morrisville, Pa.), Cy3 monoreactive NHS ester (Amersham Biosciences, Sweden), RPMI-1640 (ATCC, Manassas, Va.), heat-inactivated fetal bovine serum (Invitrogen, Carlsbad, Calif.), penicillin-streptomycin (Gibco, Carlsbad, Calif.), 11-mercaptoundecanoic acid 95% (11-MUA), 3-mercaptopropionic acid 99% (3-MPA), N-hydroxysuccinimide 97% (NHS), 1-ethyl-3-(3-(dimethylamino)-propyl) carbodiimide (EDAC), fibronectin protein, trypsin-EDTA, sigmacote, and glutaraldehyde (Sigma-Aldrich, Milwaukee, Wis.), paraformaldehyde, 4', 6-diamidino-2-phenylndole (DAPI), anti vinculin-FITC (Sigma, St. Louis, Mo.), silicon wafers of (100) orientation (Wafernet, Calif.), lipopolysaccharide, LPS (*E.-coli* 0111:B4, endotoxin unit: 500,000) (Sigma, Milwaukee, Wis.).

ALEXA FLUOR 594 phalloidin and VYBRANT Apoptosis Assay Kit #2 were obtained from Molecular Probes (Eugene, Oreg.). REDVY (518.3 Dalton) and KREDVY (806.1 Dalton) were purchased from Synpep (Dublin, Calif.). Human umbilical cord vein endothelial (HUVE) cells and cell culture supplies including EGM-2, HEPES-buffered saline, trypsin EDTA, and trypsin neutralizing solution were purchased from Clontics (Walkersville, Md.). RAW264.7 cells (murine monocyte/macrophage) were purchased from American Type Culture Collection (Manassas, Va.). The following cell culture reagents were purchased from Gibco (Carlsbad, Calif.): Trypan Blue, Fetal Bovine Serum, HBSS (Hanks Balanced Salt Solution), DMEM (Dulbecco's Modified Eagle's Medium with 4 mM L-glutamine adjusted to contain 1.5 g/L sodium bicarbonate and 4.5 g/L glucose).

All the solvents including toluene, triethylamine, and dimethylformamide were purchased from Aldrich (Milwaukee, Wis.). Absolute ethanol was deoxygenated by dry $N_2$ before use.

Example 1

Representative Cell-Patterning Arrays with Cell-Adhesion Peptides Attached to Cell-Adhesion Sites In this example, the preparation of a dry oxidized, native oxide depleted silicon surface useful in making representative cell-patterning array of the invention is described.

Substrate Preparation.

Four-inch p-type silicon substrates with (100) orientation were cleaned with piranha (hydrogen peroxide/sulfuric acid 2:5 v/v) at 120° C. for 10 minutes, dipped in HF, and rinsed with DI water thoroughly. A 1.1 µm layer of positive photoresist was then coated on the surface, and an array of 20 µm×20 µm gold squares (electrodes) spaced 60 µm apart was patterned on silicon oxide substrates by conventional microfabrication as follows. A 10 nm layer of titanium (Ti) was then deposited onto the photoresist-developed substrates at a deposition rate of 0.3 Å/s. A gold film of 100 nm in thickness was subsequently deposited onto the Ti at a deposition rate of 5 Å/s. The photoresist was dissolved in acetone and the remaining metal film was lifted off. After lift-off, the surfaces were exposed to buffered oxide etch (HF/$NH_4F$ 5:1 v/v) for 60 seconds and rinsed with DI water to remove the native oxide on silicon regions, followed by oxidation under a dry oxygen flow for 6 hours at 400° C., yielding a 60 Å oxide layer on the silicon regions. The gold-patterned silicon wafers were cut into 8 mm×8 mm slides. To minimize surface contaminants and scratches, the silicon wafers were coated with a 2 µm layer of photoresist on their polished sides before cutting.

Surface Modification.

The protective photoresist layer on gold-patterned silicon oxide substrates was removed by sonication in acetone, then in ethanol, and finally in DI water. The substrates were then placed in NANOSTRIP 2× solution ($H_2SO_5$) at room temperature for 20 minutes and dried under nitrogen, which resulted in a hydroxyl layer on the silicon oxide surfaces. The gold-patterned silicon oxide substrates were reacted with a 20 mM solution of alkane thiols of 11-mercaptoundecanoic acid (MUA) and 3-mercaptopropionic acid (MPA) (1:10 v/v) for 16 hours to create a self-assembly monolayer (SAM) on gold squares. The substrates were then exposed to PEG solution containing 3 mM methoxy-PEG-silane (M-PEG-silane) and 1% triethylamine as a catalyst in deoxygenated toluene to passivate silicon oxide. The PEG reaction proceeded at 60° C. for 18 hours in nitrogen-filled flasks that were pre-treated with Sigmacote to minimize the side reaction of PEG with the flasks. The PEG-treated surfaces were cleaned by sonication in toluene and ethanol for 5 minutes each, followed by a rinse with DI water and drying under nitrogen. The substrates with a SAM of alkane thiol on gold and methoxy-PEG-silane on silicon oxide were then immersed in an aqueous solution of 150 mM EDAC and 30 mM N-hydroxysuccinimide (NHS) for 30 minutes to attach the NHS group to the —COOH terminus of the SAMs. The substrates with NHS on gold and PEG on silicon oxide were sterilized with 70% ethanol for 15 minutes, and exposed to either fibronectin protein, REDVY, or KREDVY peptide in a phosphate buffer solution (PBVS, pH=8.2) at a concentration of 0.1 mg/ml. The reaction continued at room temperature for 1 hour. To remove loosely bound moieties from the surface after each step of surface modification, the substrate was rinsed with its original solvent and DI water, respectively.

Surface Characterization by FTIR.

Surfaces coated with fibronectin protein or peptides were characterized using a Nicolet Magna 760 fourier transform infrared (FTIR) spectroscope equipped with an FT-85 grazing angle sample compartment. FTIR absorption spectra of 750 scans were acquired at a resolution of 8 $cm^{-1}$. The system was purged with dry air for 1 hour before each data collection to remove water vapor in the sample compartment. Spectra analysis was performed using standard Nicolet and Origin software. The grazing angle FTIR adsorption spectra of surfaces modified with various coatings are shown in FIG. 6.

Cell Culture and Adhesion.

HUVE cells were cultured in EGM-2 medium supplemented with bovine brain extract (BBE), hydrocortisone, hFGF-B, VEGF, R3-IGF-1, ascorbic acid, heparin, FBS, hEGF, and GA-1000. The final serum concentration was 2%. Cells were seeded on culture flasks at passage 1 and the medium was changed after 24 hours. At 70% confluency, cells were subcultured as follows. After aspiration from culture flasks, cells were rinsed with 2-3 ml of HEPES-BSS buffer solution for 3 times, followed by incubation with 2 ml of trypsin/EDTA solution. The trypsinization process continued until about 90% of the cells were collected. After cells were released, the trypsin was neutralized in the flask with 4 ml of TNS, and the detached cells were transferred to a 15-ml sterile centrifuge tube. The harvested cells were centrifuged at 220 g for 5 minutes. Cells were diluted in growth medium. Cells at a concentration of $1.5 \times 10^5$ cells/ml were seeded on the substrates. The substrates were incubated for 18 hours before fixation with a mixture of 2% glutaraldehyde and paraformaldehyde in phosphate buffer solution for optical microscopy and with 4% paraformaldehyde for fluorescence microscopy. The optical micrographs of the cells are shown in FIGS. 7A-7C. The fluorescent images of cells are shown in FIGS. 9A-9D.

Cell Staining.

Cells adhered on the substrates were fixed, permeabilized, and stained with ALEXA FLUOR 594 phalloidin dye for F-actin staining (red) and immunostained with monoclonal anti-vinculin-FITC (green) followed by cellular staining with 6-diamidino-2-phenylIndole (DAPI, blue). Before fixation, the substrates were washed with PBS to remove cell debris and loosely attached cells. Cells were fixed with 4% paraformaldehyde in PBS for 30 minutes at room temperature and permeabilized by treating cells with Triton X100 (0.1% in PBS) for 10 minutes. Following three washes with PBS the samples were incubated for 30 minutes with a 1× blocking buffer solution (5% (w/v) of nonfat dry milk in PBS containing 0.1% Tween-20) for background passivation. The actual staining was done in two steps. First, the primary antibody against vinculin (anti vinculin-FITC) was diluted in blocking buffer following the manufacturer's recommendations and treated with cells over night in dark at 4° C. Next, the samples were washed three times with blocking buffer before cells were exposed to a phalloidin-ALEXA FLUOR 546 for 1 hour at RT. The samples were then washed with PBS three times and blown dry with air. A final treatment with gold anti-fade solution containing 6-diamidino-2-phenylIndole (DAPI) stained cell nuclei and preserved the fluorescence of the samples for confocal microscopy. The fluorescent confocal images of cells after staining are shown in FIGS. 8A-8D.

Cell Viability Assay: Apoptosis and Necrosis.

VYBRANT apoptosis assay allows for the simultaneous visualization of viable, necrotic, and apoptotic cells on substrates. Necrosis results from direct cell damage; apoptosis is genetically-programmed cell death in which cells effectively commit suicide. Green fluorescently labeled Annexin V protein (in the presence of calcium) specifically binds to the phosphatidylserine protein on membranes of apoptotic cells. Propidium iodide does not penetrate to either live or apoptotic cells, but rather, stains nuclei of necrotic cells in red. Cell-patterned substrates were washed twice with cold PBS and placed in 500 μL of Annexin V binding buffer (10 mM HEPES, 140 mM NaCl, 2.5 mM $CaCl_2$, pH 7.4). The substrates were incubated with 100 μL of Annexin V and 2 μL of PI solution for 15 minutes at room temperature, washed twice with binding buffer, and imaged with a fluorescence microscope. The fluorescence images showing the apoptotic cells and necrotic cells are shown in FIGS. 10A-10F.

Example 2

Detection of Bacterial Infection Using a Representative Cell-Patterning Array

In this example, a method for using a representative array of the invention for detecting bacterial infection is described.

Substrate Preparation.

Four inch p-type silicon substrates of (100) orientation were cleaned with piranha (hydrogen peroxide/sulfuric acid 2:5, v/v) at 120° C. for 10 minutes, dipped in HF, and thoroughly rinsed with DI water. A layer (1.1 μm) of positive photoresist was then coated on the surface, and patterns were formed on the substrate upon exposure to ultraviolet light through a mask with square patterns of three different sizes (25, 100, and 400 μm$^2$). A titanium (Ti) layer (10 nm) was then deposited on the photoresist-developed substrates at a deposition rate of 0.3 Å/s. A gold film of 100 nm thickness was subsequently deposited on the Ti at a deposition rate of 5 Å/s. The photoresist was dissolved in acetone and the remaining metal film was lifted off. After lift off, the surface was exposed to buffered oxide etch (HF/$NH_4F$ 5:1, v/v) for 60 seconds and rinsed with DI water to remove native oxide on silicon before oxidation. The surface oxidation was performed under a dry oxygen flow for 6 hours at 400° C. The gold-patterned silicon oxide substrates were then cut into slides of 8 mm×8 mm To prevent surface contamination and scratches, the silicon oxide wafers were coated with a 2 μm layer of photoresist on their polished sides before cutting.

Surface Modification.

The surface was modified following a previously established procedure with minor modifications. Veiseh, M. et al., *Langmuir* 18, 6671-6678, 2002; and Lan, S. et al., *Biosens. Bioelectron.* 20, 1697-1708, 2005. The protective photoresist layer on gold-patterned silicon substrates was removed by sonication for 10 minutes in acetone, 2 minutes in ethanol, and 2 minutes in DI water. The substrates were then placed in NANOSTRIP 2× solution ($H_2SO_5$) at room temperature for 20 minutes, and dried under nitrogen, resulting in a hydroxyl layer on the silicon oxide surface.

The gold electrodes on the substrate were first reacted with a 20 mM mixture of alkane thiols of 11-merecaptoundecanoic acid (MUA) and 3-mercaptopropionic acid (MPA) (1:10, v/v) for 16 hours to create a self-assembly monolayer (SAM). The silicon oxide background was passivated with polyethylene glycol (PEG). The PEG solution was prepared in a nitrogen-filled reaction flask by adding 3 mM M-PEG-silane in deoxygenated toluene containing 1% triethylamine as catalyst. The NANOSTRIP-treated substrate was then placed in a separate nitrogen-filled flask that was rendered hydrophobic with Sigmacote to minimize the side reaction of PEG with the flask. The PEG reaction proceeded under nitrogen at 60° C. for 18 hours. Physically adsorbed moieties were removed from the PEG-treated surface by sonication in toluene and ethanol for 5 minutes each, followed by rinsing with DI water and drying under nitrogen. The substrate with alkane thiol SAM on gold and M-PEG-silane on the silicon oxide background was immersed in an aqueous solution of 150 mM EDAC and 30 mM N-hydroxysuccinimide (NHS) for 30 minutes to attach the NHS group to the —COOH terminus of SAM. The substrate with NHS on gold and PEG on silicon oxide was sterilized with 70% ethanol for 15 minutes and exposed to fibronectin protein at a concentration of 0.05 mg/mL in a phosphate buffer solution (PBS) of pH 8.2 at room temperature for 45 minutes. To remove loosely bound moieties from the surface after each step of the surface modification, the substrate was rinsed with the original solvent and then DI water.

Cell Culture.

RAW264.7 of passage less than 10 was cultured at 37° C. in a 5% $CO_2$-humidified incubator and grown in DMEM medium supplemented with 10% (v/v) heat-inactivated FBS, 4 mM L-glutamine, 1.5 g/L sodium bicarbonate, 4.5 g/L glucose, 100 units/mL penicillin, and 100 g/mL streptomycin. Cells were subcultured by a cell scrapper once a week. Culture conditions were the same for both LPS treated and control cells on surfaces. LPS treatments were performed using a stock solution of lipopolysaccharide (500,000 endotoxin units/mg) from *E. coli* 0111:B4 in HBSS at 1 mg/mL. RAW264.7 cells at a concentration of 2.5×10$^5$ cells/mL in DMEM medium were exposed to LPS at doses of 0.1, 1, or 10 μg/mL, and 0.5 mL of solutions were incubated with the surfaces for up to 21 hours under sterile condition to avoid contamination.

Cell Viability Assay.

After cell culture, both LPS treated and un-treated (control) cell-patterned substrates were washed twice with PBS and placed in 500 μL of Annexin V binding buffer (10 mM HEPES, 140 mM NaCl, 2.5 mM $CaCl_2$, pH 7.4). The substrates were incubated with a mixture of 100 µl of Annexin V and 2 µl of propidium iodide solutions for 15 minutes at room temperature, washed twice with the binding buffer, and visualized with a fluorescence microscope. The green fluorescently labeled Annexin V protein (in the presence of calcium) specifically binds to the phosphatidylserine protein on membranes of apoptotic cells. Propidium iodide does not penetrate either live or apoptotic cells, but stains nuclei of necrotic cells in red.

Differential Interference Contrast (DIC) Reflectance Microscopy.

Cell-cultured surfaces were examined with a differential interference contrast (DIC) reflectance microscope (Nikon E800 Upright Microscope, NY, N.Y.) equipped with DIC-20x (N.A. 0.46) and DIC-50x (N.A. 0.8) objectives. Images were acquired with a Coolsnap camera (series A99G81021, Roper Scientific Inc., AZ, USA) attached to the microscope and a computer. The optical DIC images of cells after exposing to LPS at varied concentrations for 21 hours are shown in FIGS. 11A-11D and FIGS. 13B-13E. FIGS. 12A, 12C, and 12E are optical DIC images of electrodes with a single cell, double cells, and triple cells, respectively. The optical DIC images of cells stained with Annexin V and propidium iodide are shown in FIGS. 14A and 14B.

FTIR Spectromicroscopy of Cells on Patterned Substrates.

IR spectra and optical reflectance DIC images were acquired from cells on the patterned substrates with single or a group of macrophage cells on each electrode both before and after cellular exposure to LPS. Synchrotron FTIR spectra were acquired from cell-patterned surfaces with a Nicolet Magna 760 FTIR bench and a Nicolet Nic-Plan™ IR microscope equipped with a computer-controlled x-y-z sample stage (via Nicolet Atlµµs™ and OMNIC software) and an MCT-A detector at Beamline 1.4.3 of the Advanced Light Source (ALS) in Lawrence Berkeley National Laboratory, Berkeley. Calif. Martin, M. C. and McKinney, R. W., *Proceed. Mater. Res. Soc.* 524, 11-15, 1998; CA. Martin, M. C. and McKinney, R. W., *Proceedings of the Low Energy Electrodynamics in Solids, '99 Conference, Pécs, Hungary, Special Issue of Ferroelectrics,* 249, 1-10, 2001. In order to align the incident IR beam onto the substrate, an IR map (with 2-10 µm step size in x-y plane) was acquired around a gold electrode for a full IR range of 400-10,000 wave numbers. Under this condition, the whole spectrum appeared as a broad peak and an intensity profile was given for the mapped region. The x, y positions were adjusted so that the highest intensity region of the beam was aligned with the center of the gold electrode. The samples were measured at wave numbers of 650-10,000 cm$^{-1}$ using an XT-KBr beamsplitter and an MCT detector. The synchrotron infrared light is focused to a diffraction-limited spot size with a wavelength-dependent diameter of approximately 3-10 µm across the mid-IR range of interest. Carr, G. L. *Review of Scientific Instruments* 72, 1613-1619, 2001; and Dumas, P., et al., *Faraday Discussions* 126, 289-302, 2004. An on-stage temperature controlled mini incubator was used to maintain a proper environment for cellular analysis. Prior to infrared analysis, dead and loosely bound cells were removed from the substrate by three PBS washes (to eliminate the possible interference of dead and loosely bound cells to the real-time signals generated by live cells), the cell culture medium was replaced with fresh sterile medium, and the substrate covered with a layer of the medium was transferred to the mini incubator. The spectra were acquired in less than 10 minutes following the sample transfer to ensure cell viability and to minimize possible interference from environmental changes. Synchrotron FTIR spectra of 128 scans at a resolution of 8 cm$^{-1}$ were acquired from individual electrodes patterned with cells. Background signals were collected from the silicon oxide surface of the same substrate right before the data collection. Images of 75 electrodes were captured and signals from four electrodes hosting cells of similar morphologies were collected and averaged for each type of LPS treatment. All spectra were baseline-corrected and normalized to account for the continuous decay of the synchrotron beam in the storage ring. An appropriately scaled water vapor spectrum was subtracted from the spectra of cells. The spectra obtained with conventional FTIR were acquired from cell-patterned surfaces using a Thermo-Electron Nexus 870 bench and a Thermo-Electron Continuum infrared microscope with an MCT-A detector at Beamline 1.4.4 of the ALS under the same conditions set for the synchrotron measurements, except that an aperture size of 90 µm×90 µm were employed to maximize the signal intensity. The real-time synchrotron IR spectra of cells before and after treatment of LPS are shown in FIGS. 12B, 12D, and 12F. The real-time synchrotron FTIR spectra of cells treated with varied concentrations of LPS are shown in FIG. 13A. FIG. 15A shows the real-time synchrotron IR spectrum of a single cell response to LPS over time.

Example 3

Comparison of Cell-Patterning Arrays Based on Native Silicon Surface, Wet Oxide Surface, and Dry Oxide Surfaces In this example, the preparations of cell-patterning arrays based on native silicon surface, wet oxidized native oxide depleted silicon surface, and dry oxidized native oxide depleted silicon surface are described. The cellular viability and stability of these arrays are compared.

Substrate Preparation.

Four inch p-type silicon substrates of (100) orientation were cleaned with piranha (hydrogen peroxide/sulfuric acid 2:5 v/v) at 120° C. for 10 minutes, dipped in HF, and rinsed with DI water thoroughly. A layer of positive photoresist (1.1 µm) was then coated on the surface, and an array of squares (20 µm×20 µm) was patterned on the substrate upon exposure to UV light through a mask. A thin layer of titanium (Ti) of 10 nm in thickness was then deposited onto the photoresist-developed substrate at a deposition rate of 0.3 Å/s. Gold films of 100 nm in thickness were subsequently deposited on the Ti at a deposition rate of 5 Å/s. The photoresist was dissolved in acetone, and the remaining metal films were lifted off. The surface with native oxide was formed as a result of exposure of the substrates to the air. The surface with dry oxide was created by additionally exposing the surface to buffered oxide etch (HF/NH$_4$F 5:1 v/v) for 60 seconds and rinsing with DI water to remove the native oxide on silicon regions, followed by flushing with a dry oxygen flow for 6 hours at 400° C., yielding a 60 Å oxide layer on the silicon regions. The surface with wet oxide was prepared following the same procedure except that the substrates were placed under a wet oxygen flow at 850° C., yielding a 1000 Å oxide layer on the silicon regions. The gold-patterned silicon oxide wafers were cut into 8 mm×8 mm slides. To minimize surface contaminants and unexpected scratches, the silicon oxide wafers were coated with a layer of photoresist of 2 µm in thickness on their polished sides before cutting.

Surface Engineering Silicon Substrates.

Silicon substrates were washed with acetone, ethanol, and DI water before being placed in NANOSTRIP 2× at room temperature for 30 minutes, followed by an extensive rinse with DI water and passive drying under nitrogen. The substrates were then reacted with M-PEG-silane according to the following procedure. The M-PEG-silane solution was prepared in nitrogen-filled reaction flasks by adding 3 mM PEG-silane in anhydrous toluene containing 1% triethylamine as catalyst. The PEG reaction proceeded under nitrogen at 60° C. for 18 hours. Loosely bound moieties were removed from the PEG-treated surfaces by sonicating them in toluene and ethanol for 5 minutes each, followed by rinsing with DI water and drying under nitrogen.

Gold-Patterned Silicon Substrate.

The gold regions of the piranha-treated substrates were first reacted with a 20 mM mixture of alkane thiols of 11-mercaptoundecanoic acid (MUA) and 3-mercaptopropionic acid (MPA) (1:10 v/v) for 16 hours to form a self-assembly monolayer (SAM). The silicon background was passivated with PEG through the procedure described above. The substrates were then immersed in an aqueous solution of 150 mM EDAC and 30 mM N-hydroxysuccinimide (NHS) for 30 minutes to attach the NHS group to the —COOH terminus of SAM. The substrates with NHS on the gold and PEG on the silicon oxide were sterilized with 70% ethanol for 15 minutes and exposed to fibronectin protein at a concentration of 0.1 mg mL$^{-1}$ in a phosphate buffer solution (PBS) of pH 8.2 at room temperature for 45 minutes. To remove loosely bound moieties after each step of the surface modification, the substrate was rinsed with its original solvent and DI water, respectively. As a result, the immobilized protein formed a biocompatible layer on the gold arrays, and the M-PEG-silane formed an inert, biocompatible layer on the silicon oxide background, as shown in FIG. 1B.

Fluorescence Labeling of Proteins.

Fibronectin ($M_w$=440 kDa) at a concentration of 1 mg/mL in PBS (pH 8.3) was reacted with Cy3 monoreactive NHS ester ($M_w$=765.95 Da, 10 mg/mL in dimethylformamide) at a 100:1 ratio of dye to protein. The reaction proceeded in the dark for 30 minutes at room temperature with gentle stirring every 10 minutes. The unconjugated dye was separated by dialysis against PBS overnight at 4° C. using a Slide-A-Lyzer (Pierce Biotechnology, IL) membrane (exclusion limit of $M_r$=3500). Samples were diluted with PBS to a 0.1 mg/mL concentration, verified with UV spectroscopy before application to the surfaces. The UV absorbance of the solution diluted 4-fold was 0.40225 and 1.974 AU at 280 and 548 nm, respectively. Considering a molar extinction coefficient of 150 000 M$^{-1}$ cm$^{-1}$ for Cy3 dye and 563 200 M$^{-1}$ cm$^{-1}$ for fibronectin, a labeling ratio of 30.33 ([Cy3]/[fibronectin]) was detected.

Cell Culture.

Mouse macrophage (RAW 264.7) cell line was cultured in 75 cm$^2$ flasks at 37° C. in a humidified atmosphere with 5% $CO_2$. The medium contained 10% fetal bovine serum (FBS) in RPMI-1640 supplemented with 2 mM L-glutamine 50 IU mL$^{-1}$ penicillin, and 50 µg mL$^{-1}$ streptomycin. The medium was changed every third day. For cell adhesion, 0.5 mL of macrophage cells at a concentration of 2×10$^5$ cells mL$^{-1}$ was plated onto the protein-patterned substrates. The cells were allowed to adhere for 3, 7, and 10 days under the standard culture condition. The adhered cells were fixed with 2% glutaraldehyde for 20 minutes at room temperature.

X-ray Photoelectron Spectroscopy (XPS).

XPS spectra were taken on a Surface Science Instruments S-probe spectrometer. This instrument has a monochromatized Al Kα X-ray source. The X-ray spot size for these acquisitions was on the order of 800 µm. Pressure in the analytical chamber during spectral acquisition was less than 5×10$^{-9}$ torr. The pass energy for survey spectra (composition) was 150 eV, and that for high-resolution $C_{1s}$ (HRC) and $Si_{2p}$ (HRSi) scans was 50 eV. The takeoff angle (the angle between the sample normal and the input axis of the energy analyzer) was 55° (≅=50 Å sampling depth).

The Service Physics ESCAVB Graphics Viewer program was used to determine peak areas, calculate the elemental compositions from peak areas, and peak-fit the high resolution spectra. The binding energy scale of the high-resolution $C_{1s}$ spectra, shown in FIGS. 2F-2H, was calibrated by assigning the hydrocarbon peak in the $C_{1s}$ high-resolution spectrum a binding energy of 285.0 eV. The binding energy scale for the $Si_{2p}$ high-resolution spectra, shown in FIGS. 2A-2E, was calibrated to the $C_{1s}$ peak position in the survey scan.

Contact Angle Measurements.

Contact angles were measured by the sessile drop technique using a Rame-Hart 100 goniometer under ambient laboratory conditions (~40% humidity). A 2 µL drop of distilled water was applied to the surface, and the contact angle measurements were made within 30 seconds of the contact. The measurements were repeated for five samples.

Differential Interference Contrast (DIC) Reflectance Microscopy.

Cell-patterned surfaces were characterized with a differential interference contrast (DIC) reflectance microscope (Nikon E800 Upright Microscope, New York, N.Y.). Surfaces were visualized using a DIC-10× (N.A. 0.3) and DIC-50× (N. A. 0.8) objectives. Images were acquired by a CoolSNAP camera (series A99G81021, Roper Scientific Inc., AZ) attached to the microscope and a computer. FIGS. 4A-4I show the DIC reflectance microscopic images of cells cultured on the array for up to 10 days.

Fluorescence Microscopy.

Fluorescence images were acquired on a Nikon Eclipse E800 upright wide field fluorescent microscope (Nikon Instruments, Inc., Melville, N.Y.) equipped with a Photometrics CoolSNAP HQ CCD camera (Roper Scientific, Inc., Tucson, Ariz.). Surfaces were visualized using a DIC-10× (0.46) objective and rhodamine filter (excitation, 530-560 nm; emission, 590-650 nm). The amount of proteins adsorbed on surfaces was quantified by fluorescence intensity measurements. To avoid the interference from gold electrodes, the substrates without gold patterns were used. A rectangular region of interest (ROI) was selected on each image, and intensity per area was calculated and presented in arbitrary units. FIGS. 3A-3F show the fluorescent images of fibronectin-Cy3 conjugate adsorbed on surfaces patterned with gold electrodes.

While illustrative embodiments have been illustrated and described, it will be appreciated that various changes can be made therein without departing from the spirit and scope of the invention.

The invention claimed is:

1. A method for making an array for guided cell patterning, comprising:
   (a) providing a metal-patterned silicon substrate having an array of metal surfaces disposed on a silicon surface;
   (b) exposing the substrate to an oxide etch to remove native oxide from the silicon oxide surface to provide a native oxide depleted silicon surface;
   (c) oxidizing the native oxide depleted silicon surface with an oxidizing agent dry oxygen at about 300° C. to about 500° C. to provide a silicon oxide surface; and
   (d) passivating the silicon oxide surface by covalently coupling polyalkylene oxide moieties to the silicon oxide surface to provide a surface resistant to cell adhesion isolating each metal surface of the metal surface array.

2. The method of claim 1, further comprising forming a self-assembly monolayer on each metal surface to provide an array of monolayers isolated on the silicon oxide surface.

3. The method of claim 2, further comprising attaching a plurality of ligands to each self-assembly monolayer to provide an array of cell adhesion sites.

4. The method of claim 3, further comprising immobilizing a single cell at each cell adhesion site through the interaction of the ligands and one or more cell surface receptors of the cell.

5. The method of claim 3, further comprising immobilizing two or more cells at each cell adhesion site through the interaction of the ligands and one or more cell surface receptors of the cells.

6. The method of claim 1, wherein the oxide etch comprises $H_2SO_5$ or a mixture of hydrogen fluoride and ammonium fluoride.

7. The method of claim 1, wherein oxidizing the native oxide depleted surface comprises oxidizing the native oxide depleted surface with dry oxygen at about 300° C. to about 500° C. for about 5 to about 24 hours.

8. The method of claim 1, wherein the silicon oxide surface comprises from about 40% to 65% by weight Si, from about 5% to about 20% by weight $SiO_{x<2}$, and from about 20% to about 40% by weight $SiO_2$.

9. The method of claim 1, wherein the silicon oxide surface comprises from about 50% to 60% by weight Si, from about 10% to about 15% by weight $SiO_{x<2}$, and from about 25% to about 35% by weight $SiO_2$.

10. The method of claim 1, wherein the ligands are cell adhesion peptides.

11. A method for making an array of cell adhesion sites, comprising:
   (a) providing a metal-patterned silicon substrate having an array of metal surfaces disposed on a silicon surface;
   (b) exposing the substrate to an oxide etch to remove native oxide from the silicon oxide surface to provide a native oxide depleted silicon surface;
   (c) oxidizing the native oxide depleted silicon surface with an oxidizing agent dry oxygen at about 300° C. to about 500° C. to provide a silicon oxide surface;
   (d) forming a self-assembly monolayer on each metal surface to provide an array of monolayers disposed on the silicon oxide surface;
   (e) passivating the silicon oxide surface by covalently coupling polyalkylene oxide moieties to the silicon oxide surface to provide a surface resistant to cell adhesion isolating each self-assembly monolayer of the monolayer array; and
   (f) attaching a plurality of ligands to each self-assembly monolayer to provide an array of cell adhesion sites.

12. The method of claim 11, further comprising immobilizing a single cell at each cell adhesion site through the interaction of the ligands and one or more cell surface receptors of the cell.

13. The method of claim 11, further comprising immobilizing two or more cells at each cell adhesion site through the interaction of the ligands and one or more cell surface receptors of the cells.

14. The method of claim 11, wherein the metal-patterned silicon substrate comprises a p-type silicon substrate with (100) orientation having an array of metal squares patterned thereon.

15. The method of claim 11, wherein forming a self-assembly monolayer on each metal surface comprises reacting the metal surfaces with a thiol-terminated alkanoic acid to provide a carboxylic acid-terminated monolayer.

16. The method of claim 11, wherein passivating the silicon oxide surface by covalently coupling polyalkylene oxide moieties to the silicon oxide surface comprises exposing the silicon oxide surface to a reactive silane terminated-polyalkylene oxide.

17. The method of claim 11, wherein attaching a plurality of ligands to each self-assembly monolayer comprises covalently coupling the ligands to each self-assembly monolayer.

18. The method of claim 11, wherein attaching a plurality of ligands to each self-assembly monolayer comprises adsorbing the ligands to each self-assembly monolayer.

19. The method of claim 11, wherein metal surfaces are selected from the group consisting of gold, platinum, and silver surfaces.

20. The method of claim 11, wherein the ligands are cell adhesion peptides.

* * * * *

SEQUENCE LISTING

<160> NUMBER OF SEQ ID NOS: 3

<210> SEQ ID NO 1

```
<211> LENGTH: 6
<212> TYPE: PRT
<213> ORGANISM: Artificial Sequence
<220> FEATURE:
<223> OTHER INFORMATION: Synthetic

<400> SEQUENCE: 1

Lys Arg Glu Asp Val Tyr
1               5

<210> SEQ ID NO 2
<211> LENGTH: 4
<212> TYPE: PRT
<213> ORGANISM: Artificial Sequence
<220> FEATURE:
<223> OTHER INFORMATION: Synthetic

<400> SEQUENCE: 2

Lys Arg Gly Asp
1

<210> SEQ ID NO 3
<211> LENGTH: 5
<212> TYPE: PRT
<213> ORGANISM: Artificial Sequence
<220> FEATURE:
<223> OTHER INFORMATION: Synthetic

<400> SEQUENCE: 3

Arg Glu Asp Val Tyr
1               5
```